US009873892B2

(12) United States Patent
Böhm et al.

(10) Patent No.: US 9,873,892 B2
(45) Date of Patent: Jan. 23, 2018

(54) PRODUCTION OF FULLY PROCESSED AND FUNCTIONAL FACTOR X IN A FURIN-SECRETING MAMMALIAN EXPRESSION SYSTEM

(71) Applicants: Baxalta Incorporated, Bannockburn, IL (US); Baxalta GmbH, Glattpark (Opfikon) (CH)

(72) Inventors: Ernst Böhm, Vienna (AT); Franziska Horling, Gänserndorf (AT); Jadranka Koehn, Vienna (AT); Michael Dockal, Vienna (AT)

(73) Assignees: BAXALTA INCORPORATED, Bannockburn, IL (US); BAXALTA GMBH, Glattpark (Opfikon) (CH)

( * ) Notice: Subject to any disclaimer, the term of this patent is extended or adjusted under 35 U.S.C. 154(b) by 0 days.

(21) Appl. No.: 14/824,927

(22) Filed: Aug. 12, 2015

(65) Prior Publication Data

US 2016/0046957 A1 Feb. 18, 2016

Related U.S. Application Data

(60) Provisional application No. 62/036,438, filed on Aug. 12, 2014.

(51) Int. Cl.

| | |
|---|---|
| ***C12P 21/02*** | (2006.01) |
| ***C12N 15/85*** | (2006.01) |
| ***C12N 9/64*** | (2006.01) |
| ***A61K 38/48*** | (2006.01) |
| *C12N 5/07* | (2010.01) |
| *C12N 5/10* | (2006.01) |
| *C12N 5/071* | (2010.01) |
| *C12N 15/09* | (2006.01) |
| *C12N 15/12* | (2006.01) |
| *C12N 15/63* | (2006.01) |
| *C12N 15/79* | (2006.01) |
| *C12N 15/86* | (2006.01) |

(52) U.S. Cl.

CPC .......... *C12N 15/85* (2013.01); *A61K 38/4846* (2013.01); *C12N 9/6432* (2013.01); *C12N 9/6454* (2013.01); *C12Y 304/21006* (2013.01); *C12Y 304/21075* (2013.01)

(58) Field of Classification Search

None

See application file for complete search history.

(56) References Cited

U.S. PATENT DOCUMENTS

| | | | |
|---|---|---|---|
| 5,460,950 | A | 10/1995 | Barr et al. |
| 6,210,929 | B1 | 4/2001 | Schlokat et al. |

FOREIGN PATENT DOCUMENTS

| | | | |
|---|---|---|---|
| EP | 2292657 | A1 | 3/2011 |
| WO | 2001/094383 | A2 | 12/2001 |
| WO | 2008/143977 | A1 | 11/2008 |
| WO | 2012/167271 | A1 | 12/2012 |

OTHER PUBLICATIONS

Fischer et al., “Structural analysis of recombinant von Willebrand factor produced at industrial scale fermentation of transformed CHO cells co-expressing recombinant furin” 375 FEBS Letters 259-262 (1995).*

Himmelspach et al., “High Yield Expression of Recombinant Proteins Requiring Proteolytic Maturation: Use of the Endoprotease Furin” 1 Cell Engineering 85-107 (1999).*

Liu et al., “Improved Expression of Recombinant Human Factor IX by Co-expression of GGCS, VKOR and Furin” 33 Protein Journal 174-183 (2014).*

Bristol et al., Profactor IX: the propeptide inhibits binding to membrane surfaces and activation by factor XIa. Biochemistry, 33: 14136-14143 (1994).

Camire, Rodney M., Bioengineered factor Xa as a potential new strategy for hemophilia therapy. Expert Rev. Hematol., 5(2): 121-123 (2012).

Denault et al., Minireview: Furin/PACE/SPC1: a convertase involved in exocytic and endocytic processing of precursor proteins. FEBS Letters, 379: 113-116 (1996).

Himmelspach et al., A fully recombinant partial prothrombin complex effectively bypasses fVIII in vitro and in vivo. Thromb Haemost, 88: 1003-1011 (2002).

Himmelspach et al., Recombinant human factor X: high yield expression and the role of Furin in proteolytic maturation in vivo and in vitro. Thrombosis Research, vol. 97, pp. 51-67 (2000).

International Search Report and Written Opinion for International Application No. PCT/US2015/044883 filed on Aug. 12, 2015.

International Application No. PCT/US2015/044883 filed on Aug. 12, 2015.

Mitterlechner et al., Prothrombin complex concentrate and recombinant prothrombin alone or in combination with recombinant factor X and FVIIa in dilutional coagulopathy: a procine model. J Thromb Haemost, 9: 729-737 (2011).

Nakatomi et al., Combining FVIIa and FX into a mixture which imparts a unique thrombin generation potential to hemophilic plasma: an in vitro assessment of FVIIa/FX mixture as an alternative bypassing agent. Thrombosis Research, 125: 457-463 (2010).

Preininger et al., Strategies for recombinant Furin employment in a biotechnological process: complete target protein precursor cleavage. Cytotechnology, vol. 30, No. 1-3, pp. 1-15 (1999).

(Continued)

*Primary Examiner* — Nancy J Leith

(74) *Attorney, Agent, or Firm* — Wolf, Greenfield & Sacks, P.C.

(57) ABSTRACT

Disclosed herein are methods for production of fully-processed mature Factor X in an expression system producing a controlled amount of furin between 50 U/mL and 300 U/mL of culture supernatant. Also disclosed are transformed cells, expression systems, and expression vectors for the expression of furin and Factor X.

16 Claims, 14 Drawing Sheets

(56) References Cited

OTHER PUBLICATIONS

Rehemtulla et al., Preferred sequence requirements for cleavage of Pro-von Willebrand Factor by propeptdie-processing enzymes. Blood, vol. 79, No. 9, pp. 2349-2355 (1992).
Schlokat et al., Production of highly homogeneous and structurally intact recombinant von Willebrand Factor multimers by furin-mediated propeptide removal in vitro. Biotechnol. App. Biochem., 24: 257-267 (1996).
Stanton et al., Processing and expression of rat and human clotting factor-X-encoding cDNAs. Gene, 169: 269-273 (1996).
Wallin et al., Intracellular proteolytic processing of the two-chain vitamin k-dependent coagulation factor X. Thrombosis Research, vol. 73, No. 6, pp. 395-403 (1994).
Wasley et al., PACE/Furin can process the vitamin K-dependent pro-factor IX precursor within the secretory pathway. The Journal of Biological Chemistry, vol. 268, No. 12, pp. 8458-8465 (1993).
Wise et al., Expression of a human proprotein processing enzyme: correct cleavage of the von Willebrand factor precursor at a paired basic amino acid site. Proc. Natl. Acad. Sci. USA, vol. 87, pp. 9378-9382 (1990).

* cited by examiner

GACGGATCGGGAGATCTCCCGATCCCCTATGGTCGACTCTCAGTACAATCTGCTCTGATGCCGCATAGTTAAGCCAGTATCTGCTCCCT
GCTTGTGTGTTGGAGGTCGCTGAGTAGTGCGCGAGCAAAATTTAAGCTACAACAAGGCAAGGCTTGACCGACAATTGCATGAAGAATCT
GCTTAGGGTTAGGCGTTTTGCGCTGCTTCGCGATGTACGGGCCAGATATACGCGTTGACATTGATTATTGACTAGTTATTAATAGTAAT
CAATTACGGGGTCATTAGTTCATAGCCCATATATGGAGTTCCGCGTTACATAACTTACGGTAAATGGCCCGCCTGGCTGACCGCCCAAC
GACCCCCGCCCATTGACGTCAATAATGACGTATGTTCCCATAGTAACGCCAATAGGGACTTTCCATTGACGTCAATGGGTGGACTATTT
ACGGTAAACTGCCCACTTGGCAGTACATCAAGTGTATCATATGCCAAGTACGCCCCCTATTGACGTCAATGACGGTAAATGGCCCGCCT
GGCATTATGCCCAGTACATGACCTTATGGGACTTTCCTACTTGGCAGTACATCTACGTATTAGTCATCGCTATTACCATGGTGATGCGG
TTTTGGCAGTACATCAATGGGCGTGGATAGCGGTTTGACTCACGGGGATTTCCAAGTCTCCACCCCATTGACGTCAATGGGAGTTTGTT
TTGGCACCAAAATCAACGGGACTTTCCAAAATGTCGTAACAACTCCGCCCCATTGACGCAAATGGGCGGTAGGCGTGTACGGTGGGAGG
TCTATATAAGCAGAGCTCTCTGGCTAACTAGAGAACCCACTGCTTACTGGCTTATCGAAATTAATACGACTCACTATAGGGAGACCCAA
GCTGGCTAGCGTTTAAACTTAAGCTTGGTACCGAGCTCGGATCCACTAGTCCAGTGTGGTGGAATTCTGCAGATATCCAGCACAGTGGC
GGCCGCATGGAGCTGAGGCCCTGGTTGCTATGGGTGGTAGCAGCAACAGGAACCTTGGTCCTGCTAGCAGCTGATGCTCAGGGCCAGAA
GGTCTTCACCAACACGTGGGCTGTGCGCATCCCTGGAGGCCCAGCGGTGGCCAACAGTGTGGCACGGAAGCATGGGTTCCTCAACCTGG
GCCAGATCTTCGGGGACTATTACCACTTCTGGCATCGAGGAGTGACGAAGCGGTCCCTGTCGCCTCACCGCCCGCGGCACAGCCGGCTG
CAGAGGGAGCCTCAAGTACAGTGGCTGGAACAGCAGGTGGCAAAGCGACGGACTAAACGGGACGTGTACCAGGAGCCCACAGACCCCAA
GTTTCCTCAGCAGTGGTACCTGTCTGGTGTCACTCAGCGGGACCTGAATGTGAAGGCGGCCTGGGCGCAGGGCTACACAGGGCACGGCA
TTGTGGTCTCCATTCTGGACGATGGCATCGAGAAGAACCACCCGGACTTGGCAGGCAATTATGATCCTGGGGCCAGTTTTGATGTCAAT
GACCAGGACCCTGACCCCCAGCCTCGGTACACACAGATGAATGACAACAGGCACGGCACACGGTGTGCGGGGGAAGTGGCTGCGGTGGC
CAACAACGGTGTCTGTGGTGTAGGTGTGGCCTACAACGCCCGCATTGGAGGGGTGCGCATGCTGGATGGCGAGGTGACAGATGCAGTGG
AGGCACGCTCGCTGGGCCTGAACCCCAACCACATCCACATCTACAGTGCCAGCTGGGGCCCCGAGGATGACGGCAAGACAGTGGATGGG
CCAGCCCGCCTCGCCGAGGAGGCCTTCTTCCGTGGGGTTAGCCAGGGCCGAGGGGGGCTGGGCTCCATCTTTGTCTGGGCCTCGGGGAA
CGGGGGCCGGGAACATGACAGCTGCAACTGCGACGGCTACACCAACAGTATCTACACGCTGTCCATCAGCAGCGCCACGCAGTTTGGCA
ACGTGCCGTGGTACAGCGAGGCCTGCTCGTCCACACTGGCCACGACCTACAGCAGTGGCAACCAGAATGAGAAGCAGATCGTGACGACT
GACTTGCGGCAGAAGTGCACGGAGTCTCACACGGGCACCTCAGCCTCTGCCCCCTTAGCAGCCGGCATCATTGCTCTCACCCTGGAGGC
CAATAAGAACCTCACATGGCGGGACATGCAACACCTGGTGGTACAGACCTCGAAGCCAGCCCACCTCAATGCCAACGACTGGGCCACCA
ATGGTGTGGGCCGGAAAGTGAGCCACTCATATGGCTACGGGCTTTTGGACGCAGGCGCCATGGTGGCCCTGGCCCAGAATTGGACCACA
GTGGCCCCCCAGCGGAAGTGCATCATCGACATCCTCACCGAGCCCAAAGACATCGGGAAACGGCTCGAGGTGCGGAAGACCGTGACCGC
GTGCCTGGGCGAGCCCAACCACATCACTCGGCTGGAGCACGCTCAGGCGCGGCTCACCCTGTCCTATAATCGCCGTGGCGACCTGGCCA
TCCACCTGGTCAGCCCCATGGGCACCCGCTCCACCCTGCTGGCAGCCAGGCCACATGACTACTCCGCAGATGGGTTTAATGACTGGGCC
TTCATGACAACTCATTCCTGGGATGAGGATCCCTCTGGCGAGTGGGTCCTAGAGATTGAAAACACCAGCGAAGCCAACAACTATGGGAC
GCTGACCAAGTTCACCCTCGTACTCTATGGCACCGCCCCTGAGGGGCTGCCCGTACCTCCAGAAAGCAGTGGCTGCAAGACCCTCACGT

FIG. 1B

CCAGTCAGGCCTGTGTGGTGTGCGAGGAAGGCTTCTCCCTGCACCAGAAGAGCTGTGTCCAGCACTGCCCTCCAGGCTTCGCCCCCCAA
GTCCTCGATACGCACTATAGCACCGAGAATGACGTGGAGACCATCCGGGCCAGCGTCTGCGCCCCCTGCCACGCCTCATGTGCCACATG
CCAGGGGCCGGCCCTGACAGACTGCCTCAGCTGCCCCAGCCACGCCTCCTTGGACCCTGTGGAGCAGACTTGCTCCCGGCAAAGCCAGA
GCAGCCGAGAGTCCCCGCCACAGCAGCAGCCACCTCGGCTGCCCCCGGAGGTGGAGGCGGGGCAACGGCTGCGGGCAGGGCTGCTGCCC
TCACACCTGCCTGAGGTGGTGGCCGGCCTCAGCTGCGCCTTCATCGTGCTGGTCTTCGTCACTGTCTTCCTGGTCCTGCAGCTGCGCTC
TGGCTTTAGTTTTCGGGGGGTGAAGGTGTACACCATGGACCGTGGCCTCATCTCCTACAAGGGGCTGCCCCCTGAAGCCTGGCAGGAGG
AGTGCCCGTCTGACTCAGAAGAGGACGAGGGCCGGGGCGAGAGGACCGCCTTTATCAAAGACCAGAGCGCCCTCTGATCTAGAGGGCCC
GTTTAAACCCGCTGATCAGCCTCGACTGTGCCTTCTAGTTGCCAGCCATCTGTTGTTTGCCCCTCCCCCGTGCCTTCCTTGACCCTGGA
AGGTGCCACTCCCACTGTCCTTTCCTAATAAAATGAGGAAATTGCATCGCATTGTCTGAGTAGGTGTCATTCTATTCTGGGGGGTGGGG
TGGGGCAGGACAGCAAGGGGGAGGATTGGGAAGACAATAGCAGGCATGCTGGGGATGCGGTGGGCTCTATGGCTTCTGAGGCGGAAAGA
ACCAGCTGGGGCTCTAGGGGGTATCCCCACGCGCCCTGTAGCGGCGCATTAAGCGCGGCGGGTGTGGTGGTTACGCGCAGCGTGACCGC
TACACTTGCCAGCGCCCTAGCGCCCGCTCCTTTCGCTTTCTTCCCTTCCTTTCTCGCCACGTTCGCCGGCTTTCCCCGTCAAGCTCTAA
ATCGGGGCATCCCTTTAGGGTTCCGATTTAGTGCTTTACGGCACCTCGACCCCAAAAAACTTGATTAGGGTGATGGTTCACGTAGTGGG
CCATCGCCCTGATAGACGGTTTTTCGCCCTTTGACGTTGGAGTCCACGTTCTTTAATAGTGGACTCTTGTTCCAAACTGGAACAACACT
CAACCCTATCTCGGTCTATTCTTTTGATTTATAAGGGATTTTGGGGATTTCGGCCTATTGGTTAAAAAATGAGCTGATTTAACAAAAAT
TTAACGCGAATTAATTCTGTGGAATGTGTGTCAGTTAGGGTGTGGAAAGTCCCCAGGCTCCCCAGGCAGGCAGAAGTATGCAAAGCATG
CATCTCAATTAGTCAGCAACCAGGTGTGGAAAGTCCCCAGGCTCCCCAGCAGGCAGAAGTATGCAAAGCATGCATCTCAATTAGTCAGC
AACCATAGTCCCGCCCCTAACTCCGCCCATCCCGCCCCTAACTCCGCCCAGTTCCGCCCATTCTCCGCCCCATGGCTGACTAATTTTTT
TTATTTATGCAGAGGCCGAGGCCGCCTCTGCCTCTGAGCTATTCCAGAAGTAGTGAGGAGGCTTTTTTGGAGGCCTAGGCTTTTGCAAA
AAGCTCCCGGGAGCTTGTATATCCATTTTCGGATCTGATCAGCACGTGATGAAAAAGCCTGAACTCACCGCGACGTCTGTCGAGAAGTT
TCTGATCGAAAAGTTCGACAGCGTCTCCGACCTGATGCAGCTCTCGGAGGGCGAAGAATCTCGTGCTTTCAGCTTCGATGTAGGAGGGC
GTGGATATGTCCTGCGGGTAAATAGCTGCGCCGATGGTTTCTACAAAGATCGTTATGTTTATCGGCACTTTGCATCGGCCGCGCTCCCG
ATTCCGGAAGTGCTTGACATTGGGGAATTCAGCGAGAGCCTGACCTATTGCATCTCCCGCCGTGCACAGGGTGTCACGTTGCAAGACCT
GCCTGAAACCGAACTGCCCGCTGTTCTGCAGCCGGTCGCGGAGGCCATGGATGCGATCGCTGCGGCCGATCTTAGCCAGACGAGCGGGT
TCGGCCCATTCGGACCGCAAGGAATCGGTCAATACACTACATGGCGTGATTTCATATGCGCGATTGCTGATCCCCATGTGTATCACTGG
CAAACTGTGATGGACGACACCGTCAGTGCGTCCGTCGCGCAGGCTCTCGATGAGCTGATGCTTTGGGCCGAGGACTGCCCCGAAGTCCG

*FIG. 1B (cont.)*

GCACCTCGTGCACGCGGATTTCGGCTCCAACAATGTCCTGACGGACAATGGCCGCATAACAGCGGTCATTGACTGGAGCGAGGCGATGT
TCGGGGATTCCCAATACGAGGTCGCCAACATCTTCTTCTGGAGGCCGTGGTTGGCTTGTATGGAGCAGCAGACGCGCTACTTCGAGCGG
AGGCATCCGGAGCTTGCAGGATCGCCGCGGCTCCGGGCGTATATGCTCCGCATTGGTCTTGACCAACTCTATCAGAGCTTGGTTGACGG
CAATTTCGATGATGCAGCTTGGGCGCAGGGTCGATGCGACGCAATCGTCCGATCCGGAGCCGGGACTGTCGGGCGTACACAAATCGCCC
GCAGAAGCGCGGCCGTCTGGACCGATGGCTGTGTAGAAGTACTCGCCGATAGTGGAAACCGACGCCCCAGCACTCGTCCGAGGGCAAAG
GAATAGCACGTGCTACGAGATTTCGATTCCACCGCCGCCTTCTATGAAAGGTTGGGCTTCGGAATCGTTTTCCGGGACGCCGGCTGGAT
GATCCTCCAGCGCGGGGATCTCATGCTGGAGTTCTTCGCCCACCCCAACTTGTTTATTGCAGCTTATAATGGTTACAAATAAAGCAATA
GCATCACAAATTTCACAAATAAAGCATTTTTTTCACTGCATTCTAGTTGTGGTTTGTCCAAACTCATCAATGTATCTTATCATGTCTGT
ATACCGTCGACCTCTAGCTAGAGCTTGGCGTAATCATGGTCATAGCTGTTTCCTGTGTGAAATTGTTATCCGCTCACAATTCCACACAA
CATACGAGCCGGAAGCATAAAGTGTAAAGCCTGGGGTGCCTAATGAGTGAGCTAACTCACATTAATTGCGTTGCGCTCACTGCCCGCTT
TCCAGTCGGGAAACCTGTCGTGCCAGCTGCATTAATGAATCGGCCAACGCGCGGGGAGAGGCGGTTTGCGTATTGGGCGCTCTTCCGCT
TCCTCGCTCACTGACTCGCTGCGCTCGGTCGTTCGGCTGCGGCGAGCGGTATCAGCTCACTCAAAGGCGGTAATACGGTTATCCACAGA
ATCAGGGGATAACGCAGGAAAGAACATGTGAGCAAAAGGCCAGCAAAAGGCCAGGAACCGTAAAAAGGCCGCGTTGCTGGCGTTTTTCC
ATAGGCTCCGCCCCCCTGACGAGCATCACAAAAATCGACGCTCAAGTCAGAGGTGGCGAAACCCGACAGGACTATAAAGATACCAGGCG
TTTCCCCCTGGAAGCTCCCTCGTGCGCTCTCCTGTTCCGACCCTGCCGCTTACCGGATACCTGTCCGCCTTTCTCCCTTCGGGAAGCGT
GGCGCTTTCTCAATGCTCACGCTGTAGGTATCTCAGTTCGGTGTAGGTCGTTCGCTCCAAGCTGGGCTGTGTGCACGAACCCCCCGTTC
AGCCCGACCGCTGCGCCTTATCCGGTAACTATCGTCTTGAGTCCAACCCGGTAAGACACGACTTATCGCCACTGGCAGCAGCCACTGGT
AACAGGATTAGCAGAGCGAGGTATGTAGGCGGTGCTACAGAGTTCTTGAAGTGGTGGCCTAACTACGGCTACACTAGAAGGACAGTATT
TGGTATCTGCGCTCTGCTGAAGCCAGTTACCTTCGGAAAAAGAGTTGGTAGCTCTTGATCCGGCAAACAAACCACCGCTGGTAGCGGTG
GTTTTTTTGTTTGCAAGCAGCAGATTACGCGCAGAAAAAAAGGATCTCAAGAAGATCCTTTGATCTTTTCTACGGGGTCTGACGCTCAG
TGGAACGAAAACTCACGTTAAGGGATTTTGGTCATGAGATTATCAAAAAGGATCTTCACCTAGATCCTTTTAAATTAAAAATGAAGTTT
TAAATCAATCTAAAGTATATATGAGTAAACTTGGTCTGACAGTTACCAATGCTTAATCAGTGAGGCACCTATCTCAGCGATCTGTCTAT
TTCGTTCATCCATAGTTGCCTGACTCCCCGTCGTGTAGATAACTACGATACGGGAGGGCTTACCATCTGGCCCCAGTGCTGCAATGATA
CCGCGAGACCCACGCTCACCGGCTCCAGATTTATCAGCAATAAACCAGCCAGCCGGAAGGGCCGAGCGCAGAAGTGGTCCTGCAACTTT
ATCCGCCTCCATCCAGTCTATTAATTGTTGCCGGGAAGCTAGAGTAAGTAGTTCGCCAGTTAATAGTTTGCGCAACGTTGTTGCCATTG
CTACAGGCATCGTGGTGTCACGCTCGTCGTTTGGTATGGCTTCATTCAGCTCCGGTTCCCAACGATCAAGGCGAGTTACATGATCCCCC

*FIG. 1B (cont.)*

ATGTTGTGCAAAAAAGCGGTTAGCTCCTTCGGTCCTCCGATCGTTGTCAGAAGTAAGTTGGCCGCAGTGTTATCACTCATGGTTATGGC
AGCACTGCATAATTCTCTTACTGTCATGCCATCCGTAAGATGCTTTTCTGTGACTGGTGAGTACTCAACCAAGTCATTCTGAGAATAGT
GTATGCGGCGACCGAGTTGCTCTTGCCCGGCGTCAATACGGGATAATACCGCGCCACATAGCAGAACTTTAAAAGTGCTCATCATTGGA
AAACGTTCTTCGGGGCGAAAACTCTCAAGGATCTTACCGCTGTTGAGATCCAGTTCGATGTAACCCACTCGTGCACCCAACTGATCTTC
AGCATCTTTTACTTTCACCAGCGTTTCTGGGTGAGCAAAAACAGGAAGGCAAAATGCCGCAAAAAAGGGAATAAGGGCGACACGGAAAT
GTTGAATACTCATACTCTTCCTTTTTCAATATTATTGAAGCATTTATCAGGGTTATTGTCTCATGAGCGGATACATATTTGAATGTATT
TAGAAAAATAAACAAATAGGGGTTCCGCGCACATTTCCCCGAAAAGTGCCACCTGACGTC

*FIG. 1B (cont.)*

ATGGAGCTGAGGCCCTGGTTGCTATGGGTGGTAGCAGCAACAGGAACCTTGGTCCTGCTAGCAGCTGATGCTCAGGGCCAGAAGGTCTT
CACCAACACGTGGGCTGTGCGCATCCCTGGAGGCCCAGCGGTGGCCAACAGTGTGGCACGGAAGCATGGGTTCCTCAACCTGGGCCAGA
TCTTCGGGGACTATTACCACTTCTGGCATCGAGGAGTGACGAAGCGGTCCCTGTCGCCTCACCGCCCGCGGCACAGCCGGCTGCAGAGG
GAGCCTCAAGTACAGTGGCTGGAACAGCAGGTGGCAAAGCGACGGACTAAACGGGACGTGTACCAGGAGCCCACAGACCCCAAGTTTCC
TCAGCAGTGGTACCTGTCTGGTGTCACTCAGCGGGACCTGAATGTGAAGGCGGCCTGGGCGCAGGGCTACACAGGGCACGGCATTGTGG
TCTCCATTCTGGACGATGGCATCGAGAAGAACCACCCGGACTTGGCAGGCAATTATGATCCTGGGGCCAGTTTTGATGTCAATGACCAG
GACCCTGACCCCCAGCCTCGGTACACACAGATGAATGACAACAGGCACGGCACACGGTGTGCGGGGGAAGTGGCTGCGGTGGCCAACAA
CGGTGTCTGTGGTGTAGGTGTGGCCTACAACGCCCGCATTGGAGGGGTGCGCATGCTGGATGGCGAGGTGACAGATGCAGTGGAGGCAC
GCTCGCTGGGCCTGAACCCCAACCACATCCACATCTACAGTGCCAGCTGGGGCCCCGAGGATGACGGCAAGACAGTGGATGGGCCAGCC
CGCCTCGCCGAGGAGGCCTTCTTCCGTGGGGTTAGCCAGGGCCGAGGGGGGCTGGGCTCCATCTTTGTCTGGGCCTCGGGGAACGGGGG
CCGGGAACATGACAGCTGCAACTGCGACGGCTACACCAACAGTATCTACACGCTGTCCATCAGCAGCGCCACGCAGTTTGGCAACGTGC
CGTGGTACAGCGAGGCCTGCTCGTCCACACTGGCCACGACCTACAGCAGTGGCAACCAGAATGAGAAGCAGATCGTGACGACTGACTTG
CGGCAGAAGTGCACGGAGTCTCACACGGGCACCTCAGCCTCTGCCCCCTTAGCAGCCGGCATCATTGCTCTCACCCTGGAGGCCAATAA
GAACCTCACATGGCGGGACATGCAACACCTGGTGGTACAGACCTCGAAGCCAGCCCACCTCAATGCCAACGACTGGGCCACCAATGGTG
TGGGCCGGAAAGTGAGCCACTCATATGGCTACGGGCTTTTGGACGCAGGCGCCATGGTGGCCCTGGCCCAGAATTGGACCACAGTGGCC
CCCCAGCGGAAGTGCATCATCGACATCCTCACCGAGCCCAAAGACATCGGGAAACGGCTCGAGGTGCGGAAGACCGTGACCGCGTGCCT
GGGCGAGCCCAACCACATCACTCGGCTGGAGCACGCTCAGGCGCGGCTCACCCTGTCCTATAATCGCCGTGGCGACCTGGCCATCCACC
TGGTCAGCCCCATGGGCACCCGCTCCACCCTGCTGGCAGCCAGGCCACATGACTACTCCGCAGATGGGTTTAATGACTGGGCCTTCATG
ACAACTCATTCCTGGGATGAGGATCCCTCTGGCGAGTGGGTCCTAGAGATTGAAAACACCAGCGAAGCCAACAACTATGGGACGCTGAC
CAAGTTCACCCTCGTACTCTATGGCACCGCCCCTGAGGGGCTGCCCGTACCTCCAGAAAGCAGTGGCTGCAAGACCCTCACGTCCAGTC
AGGCCTGTGTGGTGTGCGAGGAAGGCTTCTCCCTGCACCAGAAGAGCTGTGTCCAGCACTGCCCTCCAGGCTTCGCCCCCCAAGTCCTC
GATACGCACTATAGCACCGAGAATGACGTGGAGACCATCCGGGCCAGCGTCTGCGCCCCCTGCCACGCCTCATGTGCCACATGCCAGGG
GCCGGCCCTGACAGACTGCCTCAGCTGCCCCAGCCACGCCTCCTTGGACCCTGTGGAGCAGACTTGCTCCCGGCAAAGCCAGAGCAGCC
GAGAGTCCCCGCCACAGCAGCAGCCACCTCGGCTGCCCCCGGAGGTGGAGGCGGGGCAACGGCTGCGGGCAGGGCTGCTGCCCTCACAC
CTGCCTGAGGTGGTGGCCGGCCTCAGCTGCGCCTTCATCGTGCTGGTCTTCGTCACTGTCTTCCTGGTCCTGCAGCTGCGCTCTGGCTT
TAGTTTTCGGGGGGTGAAGGTGTACACCATGGACCGTGGCCTCATCTCCTACAAGGGGCTGCCCCCTGAAGCCTGGCAGGAGGAGTGCC
CGTCTGACTCAGAAGAGGACGAGGGCCGGGGCGAGAGGACCGCCTTTATCAAAGACCAGAGCGCCCTCTGA

*FIG. 2*

MELRPWLLWVVAATGTLVLLAADAQGQKVFTNTWAVRIPGGPAVANSVARKHGFLNLGQIFGDYYHFWHRGVTKRSLSPHRPRHSRLQR
EPQVQWLEQQVAKRRTKRDVYQEPTDPKFPQQWYLSGVTQRDLNVKAAWAQGYTGHGIVVSILDDGIEKNHPDLAGNYDPGASFDVNDQ
DPDPQPRYTQMNDNRHGTRCAGEVAAVANNGVCGVGVAYNARIGGVRMLDGEVTDAVEARSLGLNPNHIHIYSASWGPEDDGKTVDGPA
RLAEEAFFRGVSQGRGGLGSIFVWASGNGGREHDSCNCDGYTNSIYTLSISSATQFGNVPWYSEACSSTLATTYSSGNQNEKQIVTTDL
RQKCTESHTGTSASAPLAAGIIALTLEANKNLTWRDMQHLVVQTSKPAHLNANDWATNGVGRKVSHSYGYGLLDAGAMVALAQNWTTVA
PQRKCIIDILTEPKDIGKRLEVRKTVTACLGEPNHITRLEHAQARLTLSYNRRGDLAIHLVSPMGTRSTLLAARPHDYSADGFNDWAFM
TTHSWDEDPSGEWVLEIENTSEANNYGTLTKFTLVLYGTAPEGLPVPPESSGCKTLTSSQACVVCEEGFSLHQKSCVQHCPPGFAPQVL
DTHYSTENDVETIRASVCAPCHASCATCQGPALTDCLSCPSHASLDPVEQTCSRQSQSSRESPPQQQPPRLPPEVEAGQRLRAGLLPSH
LPEVVAGLSCAFIVLVFVTVFLVLQLRSGFSFRGVKVYTMDRGLISYKGLPPEAWQEECPSDSEEDEGRGERTAFIKDQSAL

*FIG. 3*

PRODUCTION OF FULLY PROCESSED AND FUNCTIONAL FACTOR X IN A FURIN-SECRETING MAMMALIAN EXPRESSION SYSTEM

CROSS REFERENCE TO RELATED APPLICATIONS

The present application claims the benefit under 35 U.S.C. 119(e) to U.S. Provisional Patent Application 62/036,438, filed Aug. 12, 2014, the entire contents of which are incorporated by reference herein.

FIELD

Disclosed herein are expression systems, transformed cells, and methods related thereto, for expression of fully-processed and active recombinant Factor X in the presence of furin.

BACKGROUND

Human coagulation Factor X (FX), activated FX (FXa), and variants thereof, are used as therapeutic agents in blood coagulation disorders including, but not limited to, hemophilia and von Willebrand disease. FX, a vitamin K-dependent serine protease, is synthesized as a single chain precursor protein in the endoplasmic reticulum, with subsequent intracellular proteolytic furin cleavage in the Golgi apparatus before secretion by the producing cell into the blood stream, or into the culture medium in case of recombinant expression. Three furin cleavage sites in FX are responsible for proper FX proteolytic processing. The mature form of FX is a disulfide-linked two-chain molecule consisting of a heavy and light chain, formed after cleavage of the precursor protein. Further modifications of the molecule include γ-carboxylation of the light chain and N- and O-linked glycosylation of the activation peptide which is attached to the heavy chain.

Besides FX, further Vitamin K-dependent coagulation factors bearing the consensus recognition site Arg-X-Lys/Arg-Arg (SEQ ID NO:4) are substrates of the ubiquitously expressed endoprotease furin, also known as paired basic amino acid residue-cleaving enzyme (PACE). Adequate proteolytic processing of recombinant proteins of the coagulation cascade are impaired in cell culture expression systems due to intracellular processing limitations at high yield expression. Similar to von Willebrand Factor and coagulation Factor IX (FIX) which exhibit insufficient proteolytic processing at high expression rates in recombinant mammalian cells, FX secretion in low producing CHO cell clones is characterized by fully processed FX, whereas high producing clones comprise unprocessed single chain FX and multiple unprocessed forms of FX light chain, in addition to the correctly processed FX heavy and light chain species. Types and degrees of unprocessed FX light chain varied among individual cell clones and under different cell culture conditions such as cell density. Additional in vivo furin co-expression or post-cell culture in vitro furin incubation is needed to support the endogenous furin proteolytic machinery, facilitating intact protein cleavage.

Furin co-expression is indispensable for the expression of fully processed FX at high yield. However, to date no threshold level of furin has been reported that would ensure a high percentage of intact processed FX in cell culture systems. High levels of furin are toxic, therefore levels of furin expression by FX-producing mammalian expression systems must be balanced between levels that are toxic, yet potentially process 100% of the FX precursor protein, and those that are too low, resulting in healthy cell cultures in which suboptimal processed FX is produced.

SUMMARY

Disclosed herein is a system for expressing furin and a human Factor X (FX) in the same cell line and thereby providing a critical furin concentration in the culture supernatant for the generation of fully processed and fully active FX, while maintaining the viability of the culture.

Thus, disclosed herein is a transformed cell comprising a nucleotide sequence encoding a human furin, such that the transformed cell expresses and secretes functional furin into a culture supernatant, wherein the functional furin is secreted at a concentration of about 50 U/mL to about 300 U/mL in the culture supernatant after culture for between about 36 and about 78 hours. In one embodiment, the transformed cells further comprise a nucleotide sequence encoding a protein cleavable by furin and exhibiting an Arg-(Lys/Arg)-Arg motif. In another embodiment, the nucleotide sequence encoding human furin and the nucleotide sequence encoding the protein are on different expression vectors. In another embodiment, the nucleotide sequence encoding human furin and the nucleotide sequence encoding the protein are on the same expression vector.

Also provided is a eukaryotic protein expression system comprising a cell line suitable for expression of mammalian proteins; a first expression vector adapted for expression of human furin by the cell line, wherein the first expression vector includes a nucleotide sequence encoding a human furin polypeptide; and a second expression vector adapted for expression of a protein by the cell line, wherein the second expression vector includes a nucleotide sequence encoding a protein cleavable by furin and exhibiting an Arg-(Lys/Arg)-Arg motif, wherein the cell line is capable of secreting functional furin into the culture supernatant at a concentration of about 50 U/mL to about 300 U/mL after culture for between about 36 and about 78 hours.

Also provided is a eukaryotic protein expression system comprising a cell line suitable for expression of mammalian proteins; a first expression vector adapted for expression of human furin and a protein cleavable by furin, and exhibiting an Arg-(Lys/Arg)-Arg motif, by the cell line, wherein the first expression vector includes a nucleotide sequence encoding a human furin polypeptide and a nucleotide sequence encoding the protein cleavable by furin, wherein the cell line is capable of secreting functional furin into the culture supernatant at a concentration of about 50 U/mL to about 300 U/mL after culture for between about 36 and about 78 hours. In one embodiment, the nucleotide sequence encoding human furin and the nucleotide sequence encoding the protein are on different expression vectors. In another embodiment, the nucleotide sequence encoding human furin and the nucleotide sequence encoding the protein are on the same expression vector.

Also provided is a transformed cell comprising a first nucleotide sequence encoding a human furin and a second nucleotide sequence encoding a human FX, such that the transformed cell expresses and secretes functional furin and FX into a culture supernatant, wherein the furin is secreted at a concentration of about 50 U/mL to about 300 U/mL in the culture supernatant after culture for between about 36 and about 78 hours and at least 85% of the FX is fully processed. In one embodiment, the nucleotide sequence encoding human furin and the nucleotide sequence encoding the FX are on different expression vectors. In another embodiment, the nucleotide sequence encoding human furin and the nucleotide sequence encoding the FX are on the same expression vector.

Also provided is a eukaryotic protein expression system comprising a cell line suitable for expression of mammalian proteins; a first expression vector adapted for expression of human furin by the cell line, wherein the first expression vector includes a nucleotide sequence encoding a human furin polypeptide; and a second expression vector adapted for expression of FX by the cell line, wherein the second expression vector includes a nucleotide sequence encoding FX, wherein the cell line is capable of secreting functional furin into the culture supernatant at a concentration of about 50 U/mL to about 300 U/mL after culture for between about 36 and about 78 hours.

Further provided is a eukaryotic protein expression system comprising a cell line suitable for expression of mammalian proteins; a first expression vector adapted for expression of human furin and FX, wherein the first expression vector includes a nucleotide sequence encoding a human furin polypeptide and a nucleotide sequence encoding FX, wherein the cell line is capable of secreting functional furin into the culture supernatant at a concentration of about 50 U/mL to about 300 U/mL after culture for between about 36 and about 78 hours.

Also provided is a method of preparing a recombinant protein comprising transfecting a cell line suitable for expression of mammalian proteins with a first expression vector adapted for expression of human furin by the cell line, wherein the first expression vector includes a nucleotide sequence encoding a human furin polypeptide; and transfecting the cell line with a second expression vector adapted for expression of a protein by the cell line, wherein the second expression vector includes a nucleotide sequence encoding a protein exhibiting an Arg-(Lys/Arg)-Arg motif; wherein the cell line transfected with the first and the second expression vectors expresses and secretes functional human furin at a concentration of about 50 U/mL to about 300 U/mL in the culture supernatant after culture for between about 40 and about 80 hours or about 36 and about 78 hours. In one embodiment, the cell line is transfected with the first expression vector and the second expression vector substantially simultaneously. In another embodiment, the cell line is transfected with the first expression vector and cells secreting stable levels of furin are obtained prior to transfecting the cell line with the second expression vector. In yet another embodiment, the cell line is transfected with the second expression vector and cells secreting stable levels of the protein are obtained prior to transfecting the cell line with the first expression vector.

In one embodiment, the protein is von Willebrand Factor, Factor II, Factor IX, Factor X, Protein C, Protein S, or Protein Z. In another embodiment, the protein is Factor X.

Also provided is a method of preparing a recombinant protein comprising transfecting a cell line suitable for expression of mammalian proteins with a first expression vector adapted for expression of human furin by the cell line, wherein the first expression vector includes a nucleotide sequence encoding a human furin polypeptide; and transfecting the cell line with a second expression vector adapted for expression of FX by the cell line, wherein the second expression vector includes a nucleotide sequence encoding a FX polypeptide; wherein the cell line transfected with the first and the second expression vectors expresses and secretes functional human furin at a concentration of about 50 U/mL to about 300 U/mL in the culture supernatant after culture for between about 36 and about 78 hours. In one embodiment, the cell line is transfected with the first expression vector and the second expression vector substantially simultaneously. In another embodiment, the cell line is transfected with the first expression vector and cells secreting stable levels of furin are obtained prior to transfecting the cell line with the second expression vector. In yet another embodiment, the cell line is transfected with the second expression vector and cells secreting stable levels of the protein are obtained prior to transfecting the cell line with the first expression vector.

In another embodiment, the cells are capable of secreting functional furin into the culture supernatant at a concentration of at least about 50 to about 60 U/mL after culture for between about 36 and about 78 hours and wherein at least 90% of the FX is fully processed. In another embodiment, the cells are capable of secreting functional furin into the culture supernatant at a concentration of at least about 90 to about 100 U/mL after culture for between about 36 and about 78 hours and wherein at least 95% of the FX is fully processed.

Also provided is a recombinant FX produced by a transformed cell disclosed herein.

Further provided is a recombinant FX produced by an expression system disclosed herein.

Also provided is a recombinant FX produced by a method disclosed herein.

Also provided is an expression system for recombinant FX adapted to secrete furin into a culture supernatant at a concentration of between about 50 U/mL and about 300 U/mL after culture for between about 36 and about 78 hours.

Also provided is a method of producing mature, fully-processed FX comprising an expression system secreting furin into a culture supernatant at a concentration between about 50 U/mL and about 300 U/mL after culture for between about 36 and about 78 hours.

BRIEF DESCRIPTION OF THE DRAWINGS

FIG. 1B depicts the nucleotide sequence of the vector (SEQ ID NO:1). The human furin sequence is underlined and the start and stop codons are double underlined.

FIG. 2 depicts the nucleotide sequence of human furin (SEQ ID NO:2). Start and stop codons are double underlined.

FIG. 3 depicts the amino acid sequence of human furin (SEQ ID NO:3).

FIG. 7A depicts residual of response versus predicted response where data points are scattered symmetrically around zero indicating no systematic trend. FIG. 7B depicts a normal Q-Q plot for the residuals indicating that the assumption of normal distributed errors hold as data points are scattered around the line of identity. FIG. 7C depicts residual of response versus cell line where data points are scattered symmetrically around zero indicating no systematic trend. FIG. 7D depicts observed and predicted values plotted against each other indicating a good fit of the data as the data points are scattered symmetrically around the line of identity.

DETAILED DESCRIPTION

Figure 1A:
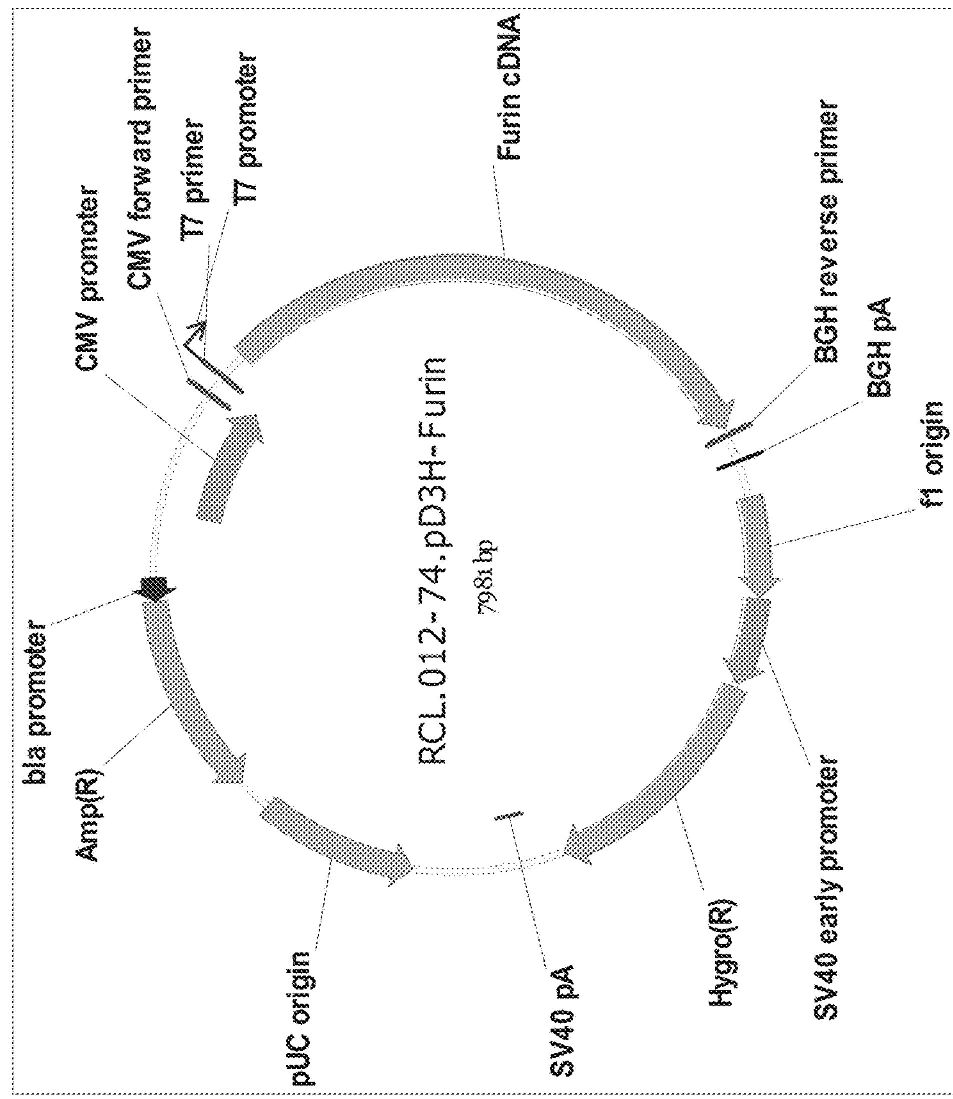
FIG. 1A depicts the RCL.012-74.pD3H-Furin expression vector

Provided herein are transformed cells, eukaryotic expression systems, methods for producing recombinant proteins, and recombinant proteins made by the methods, all directed to expression of furin and Factor X (FX) in the same cell line and thereby providing a critical furin concentration in the culture supernatant for the generation of fully processed and mature FX, while maintaining the viability of the culture.

Common to the transformed cells, eukaryotic expression systems and methods for production of recombinant proteins is the ability of the host cell to produce consistent levels of recombinant furin. Furin is necessary for cleavage of certain mammalian proteins, including FX, from a precursor protein form to a mature, fully processed form. Low concentrations of furin in the culture supernatant of the expression system result in accumulation of propeptide-containing and other non- or partially-processed forms of the protein. Concentrations of furin that are too high result in impaired growth of the host cells and ultimately cell death.

As used herein, the term "furin" includes full-length furin as well as any furin fragment capable of cleavage of the consensus recognition site Arg-X-Lys/Arg-Arg. Active truncated forms of furin are known in the art and are suitable for use in the instant disclosure, Non-limiting examples of suitable furin fragments can be found in U.S. Pat. No. 6,210,926 and Preininger et al. (Cytotechnology 30:1-15, 1999), both of which are incorporated by reference herein for all they disclose regarding truncated forms of recombinant furin.

Also within the scope of the present disclosure are variants of the furin and Factor X proteins disclosed herein. For example, conservative amino acid changes may be made, which although they alter the primary sequence of the protein or peptide, do not normally alter its function. Conservative amino acid substitutions typically include substitutions within the following groups: glycine, alanine; valine, isoleucine, leucine; aspartic acid, glutamic acid; asparagine, glutamine; serine, threonine; and lysine, arginine; phenylalanine, tyrosine.

Also included are fusion proteins, or other modifications, or FX which have increased half-life after administration to a subject. Examples of such would be fusions with an immunoglobulin Fc domain, an albumin domain, an extended (XTEN) recombinant polypeptide (see U.S. Pat. No. 8,673,860 which is incorporated by reference herein for all it discloses regarding XTEN polypeptides), poly Glu or poly Asp sequences, transferrin, or a PAS (Pro Ala Ser)-containing polypeptides attached to the FX sequence.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g. by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine. Proteins can also be modified chemically after purification with water soluble biocompatible polymers, e.g., polyethylene gycol, polysialic acid, or hydroxyethyl starch.

Also included are polypeptides which have been modified using ordinary molecular biological techniques so as to improve their resistance to proteolytic degradation or to optimize solubility properties. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The disclosure herein is generally directed to systems, transformed cells, expression vectors, and methods for producing at least one recombinant mammalian protein which is post-translationally processed by furin (a recombinant furin-requiring mammalian protein). The mammalian protein is one or more of von Willebrand Factor, Factor II, Factor IX, Factor X, Protein C, Protein S, or Protein Z. In another embodiment, the protein is FX.

The concentration of furin in the culture supernatant is targeted within an optimum range for production of mature, fully-processed proteins while maintaining viability of the culture after a defined period of culture. Thus, a useful concentration of furin in a culture supernatant for the production of a mature, fully-processed mammalian protein is between about 50 U/mL and about 400 U/mL, between about 50 U/mL and about 350 U/mL, between about 50 U/mL and about 300 U/mL, between about 50 U/mL and about 250 U/mL, between about 50 U/mL and about 200 U/mL, between about 50 U/mL and about 175 U/mL, between about 50 U/mL and about 150 U/mL, between about 50 U/mL and about 125 U/mL, or between about 50 U/mL and about 100 U/mL. In one embodiment, the concentration of furin in the culture supernatant is not less than 50 U/mL.

In other embodiment, the useful concentration of furin in the culture supernatant for the production of a mature, fully-processed mammalian protein after a defined period of culture is between about 50 U/mL and about 60 U/mL, between about 55 U/mL and about 65 U/mL, between about 60 U/mL and about 70 U/mL, between about 65 U/mL and about 75 U/mL, between about 70 U/mL and about 80

U/mL, between about 75 U/mL and about 85 U/mL, between about 80 U/mL and about 90 U/mL, between about 85 U/mL and about 95 U/mL, between about 90 U/mL and about 95 U/mL, between about 95 U/mL and about 105 U/mL, between about 100 U/mL and about 110 U/mL, between about 115 U/mL and about 125 U/mL, between about 120 U/mL and about 130 U/mL, between about 125 U/mL and about 135 U/mL, between about 130 U/mL and about 140 U/mL, between about 135 U/mL and about 145 U/mL, between about 140 U/mL and about 150 U/mL, between about 145 U/mL and about 155 U/mL, between about 150 U/mL and about 160 U/mL, between about 155 U/mL and about 165 U/mL, between about 160 U/mL and about 170 U/mL, between about 165 U/mL and about 175 U/mL, between about 170 U/mL and about 180 U/mL, between about 175 U/mL and about 185 U/mL, between about 180 U/mL and about 190 U/mL, between about 185 U/mL and about 195 U/mL, or between about 190 U/mL and about 200 U/mL. In another embodiment, the useful concentration of furin in the culture supernatant for the production of a mature, fully-processed mammalian protein after a defined period of culture is between about 50 U/mL and about 60 U/mL, or about 57 U/mL. In another embodiment, the useful concentration of furin in the culture supernatant for the production of a mature, fully-processed mammalian protein is between about 90 U/mL and about 100 U/mL, or about 96 U/mL.

In other embodiments, the useful concentration of furin in the culture supernatant for the production of a mature, fully-processed mammalian protein after a defined period of culture is less than about 400 U/mL, less than about 375 U/mL, less than about 350 U/mL, less than about 325 U/mL, less than about 300 U/mL, less than about 275 U/mL, less than about 250 U/mL, less than about 225 U/mL, less than about 200 U/mL, less than about 175 U/mL, less than about 150 U/mL, less than about 125 U/mL, or less than about 100 U/mL.

In other embodiments, the useful concentration of furin in the culture supernatant for the production of a mature, fully-processed mammalian protein after a defined period of culture is more than about 50 U/mL, more than about 60 U/mL, more than about 70 U/mL, more than about 80 U/mL, more than about 90 U/mL, more than about 100 U/mL, more than about 110 U/mL, more than about 120 U/mL, more than about 130 U/mL, more than about 140 U/mL, more than about 150 U/mL, more than about 160 U/mL, more than about 170 U/mL, more than about 180 U/mL, more than about 190 U/mL, or more than about 200 U/mL.

For the purposes of the present disclosure, the levels of furin in culture supernatants disclosed herein are generated within a period of time from about 12 hours to about 96 hours after the initiation of the culture (after culture for about 12 hours to about 96 hours) and reflect the levels of furin which accumulate in the culture supernatant during that period. In other embodiments, the desired levels of furin in culture supernatants are reached within about 18 hours to about 90 hours, about 24 hours to about 84 hours, about 30 hours to about 78 hours, about 36 to about 72 hours, about 40 hours to about 80 hours, about 42 hours to about 68 hours, or about 48 hours to about 72 hours after the initiation of the culture, or after culture for the indicated period of time.

Alternatively, the levels of furin in culture supernatants disclosed herein are expressed as a concentration of furin secreted by a quantity of cells per volume of culture supernatant per day. In a non-limiting example, the concentration of furin is expressed as U/$10^6$ cells/day. In other embodiment, a useful concentration of furin in the culture supernatant for the production of a mature, fully-processed mammalian protein is between about 20 U/$10^6$ cells/day and about 75 U/$10^6$ cells/day, between about 25 U/$10^6$ cells/day and about 75 U/$10^6$ cells/day, between about 30 U/$10^6$ cells/day and about 75 U/$10^6$ cells/day, between about 35 U/$10^6$ cells/day and about 75 U/$10^6$ cells/day, between about 40 U/$10^6$ cells/day and about 75 U/$10^6$ cells/day, between about 45 U/$10^6$ cells/day and about 75 U/$10^6$ cells/day, between about 50 U/$10^6$ cells/day and about 75 U/$10^6$ cells/day, between about 55 U/$10^6$ cells/day and about 75 U/$10^6$ cells/day, between about 60 U/$10^6$ cells/day and about 75 U/$10^6$ cells/day, between about 20 U/$10^6$ cells/day and about 70 U/$10^6$ cells/day, between about 20 U/$10^6$ cells/day and about 65 U/$10^6$ cells/day, between about 20 U/$10^6$ cells/day and about 60 U/$10^6$ cells/day, between about 20 U/$10^6$ cells/day and about 55 U/$10^6$ cells/day, between about 25 U/$10^6$ cells/day and about 55 U/$10^6$ cells/day, between about 25 U/$10^6$ cells/day and about 50 U/$10^6$ cells/day, between about 25 U/$10^6$ cells/day and about 45 U/$10^6$ cells/day, or between about 25 U/$10^6$ cells/day and about 40 U/$10^6$ cells/day.

The concentration of furin in the culture supernatant is sufficient to process at least about 75% of the mammalian precursor protein to a mature, functional protein. The protein is any protein translated as a precursor protein and processed into a mature form, at least in part, by the actions of furin. In one embodiment, the protein is FX. In other embodiments, the furin concentration is sufficient to process at least about 80% of the mammalian FX precursor protein to a mature, functional FX protein, to process at least about 82% of the mammalian FX precursor protein to a mature, functional FX protein, to process at least about 84% of the mammalian FX precursor protein to a mature, functional FX protein, to process at least about 86% of the mammalian FX precursor protein to a mature, functional FX protein, to process at least about 88% of the mammalian FX precursor protein to a mature, functional FX protein, to process at least about 90% of the mammalian FX precursor protein to a mature, functional FX protein, to process at least about 92% of the mammalian FX precursor protein to a mature, functional FX protein, to process at least about 93% of the mammalian FX precursor protein to a mature, functional FX protein, to process at least about 94% of the mammalian FX precursor protein to a mature, functional FX protein, to process at least about 95% of the mammalian FX precursor protein to a mature, functional FX protein, to process at least about 96% of the mammalian FX precursor protein to a mature, functional FX protein, to process at least about 97% of the mammalian FX precursor protein to a mature, functional FX protein, to process at least about 98% of the mammalian FX precursor protein to a mature, functional FX protein, to process at least about 99% of the mammalian FX precursor protein to a mature, functional FX protein, or to process 100% of the mammalian FX precursor protein to a mature, functional FX protein.

As used herein, the term "precursor protein" refers to a precursor protein that is inactive and is turned into an active form by cleavage and, optionally, other post-translational modifications in the cell after synthesis.

Thus, provided herein are transformed cells adapted for secretion of both furin and a mammalian protein, such as FX. The transformed cells can be any eukaryotic cell suitable for secretion of mammalian proteins, regardless of whether the cells produce endogenous furin. Suitable cell lines for generation of the transformed cells include, but are not limited to, Chinese hamster ovary (CHO) cells, human embryonic kidney cells, primate kidney cells (e.g., COS cells, HEK293), fibroblasts (e.g., murine fibroblasts), and mouse myeloma cells (e.g., NSO-GS). Suitable cell lines are capable of high level expression of mammalian proteins and are capable of post-translational modifications, e.g., glycosylation, formation of disulfide bonds, phosphorylation, and γ-carboxylation. Methods for selecting and culturing host cells and for inducing the host cells to express a polypeptide are generally known to the person skilled in the art.

Also disclosed herein are expression systems comprising cells suitable for production of mammalian proteins and at least one expression vector adapted for expression of at least one mammalian protein. Eukaryotic expression vectors are generally available for expression in mammalian cells. In order to enable furin and a mammalian protein, such as FX, to be expressed according to the methods disclosed herein, nucleotide sequences encoding the proteins are introduced into a eukaryotic cell by means of transfection, transformation or infection with an expression vector, whereby the polypeptides are expressed. The expression of the furin and/or mammalian proteins can be either transient or stable. The furin and mammalian nucleotide sequences are present as a plasmid, or as a part of a viral or non-viral expression vector. Particularly suitable viral vectors include, but are not limited to, baculoviruses, vaccinia viruses, adenoviruses, cytomegaloviruses, adeno-associated viruses, replication-competent lentiviruses (RCL), and herpes viruses. Non-limiting examples of viral eukaryotic expression vectors include Rc/CMV, Rc/RSV, RCL, and SV40 vectors. Exemplary non-viral eukaryotic expression vectors include, but are not limited to, virosomes, liposomes, cationic lipids, plasmids, and polylysine-conjugated DNA. Exemplary plasmid expression vectors include, but are not limited to, pSLX, pcDNA, and others known to persons of ordinary skill in the art.

In another embodiment, disclosed herein is an expression vector comprising a furin-encoding nucleotide sequence, a mammalian protein-encoding nucleotide sequence, such as an FX-encoding nucleotide sequence, or a combination thereof. In one embodiment, both the furin and the protein sequences are expressed from a single expression vector. In another embodiment, the furin sequence and the protein sequences are expressed from different expression vectors. In one embodiment, if the furin and protein nucleotide sequences are expressed from the same expression vector, they are optionally separated by an internal ribosome entry site (IRES). The genes can be expressed from one or more promoters. Furthermore, nucleotide sequences encoding for each protein can be oriented in opposite directions on the plasmid or oriented in the same direction. The expression vectors further comprise selectable elements and other regulatory sequences for effective production of mammalian proteins as is understood by persons of ordinary skill in the art.

Also disclosed herein are expression vectors that allow expression of furin and other mammalian proteins by use of recombinase-mediated cassette exchange.

If furin and the mammalian protein are expressed from different expression vectors, then the expression vectors will have different selection markers so that cells transformed with the vector can be selected. Such selected cells may then be isolated and grown into monoclonal cultures Promoters which permit constitutive, regulatable, tissue-specific, cell type-specific, cell cycle-specific, or metabolism-specific expression in eukaryotic cells are suitable, for example, for expression in mammalian cells. Regulatable elements are promoters, activator sequences, enhancers, silencers and/or repressor sequences. Examples of regulatable elements which permit constitutive expression in eukaryotes are promoters which are recognized by RNA polymerase III or viral promoters, cytomegalovirus (CMV) enhancer, CMV promoter, SV40 promoter or long terminal repeat (LTR) promoters, e.g. derived from MMTV (mouse mammary tumor virus) and other viral promoter and activator sequences which are derived from, for example, hepatitis B virus (HBV), hepatitis C virus (HCV), herpes simplex virus (HSV), human papilloma virus (HPV), Epstein-Barr virus (EBV), heat hock promoters, or human immunodeficiency virus (HIV). Examples of regulatable elements which permit inducible expression in eukaryotes are the tetracycline operator in combination with an appropriate repressor. The expression of furin and mammalian protein nucleotide sequences can also take place under the control of tissue-specific, or protein-specific, promoters. Non-limiting examples of protein-specific promoters are FX gene promoters or furin gene promoters.

In certain embodiments, the cells are transformed with another protein in addition to furin and the mammalian protein. In one embodiment, the additional protein is vitamin K epoxide reductase (VKOR). In certain embodiments, the additional protein is expressed from the same expression vector as one, or both, of furin and the mammalian protein, or the additional protein is expressed from a different expression vector.

Also disclosed herein are expression systems comprising host cells and one or more expression vectors adapted to express furin and at least one additional mammalian protein, e.g. FX.

Also disclosed herein are methods of producing fully processed recombinant furin-requiring mammalian proteins, such as FX. In one embodiment, a stable, recombinant furin-producing cell line is produced and subsequently transfected with an expression vector containing the nucleotide sequence for at least one furin-requiring mammalian protein. Stable, recombinant furin-producing cell lines can be established and stored for transfection with an expression vector containing the nucleotide sequence for at least one furin-requiring mammalian protein as needed. Alternatively, expression vectors for furin and for the furin-requiring mammalian protein, such as FX, can be transfected into the host cells within about 30 minutes, about 60 minutes, about 2 hours, about 6 hours, about 12 hours, or about 24 hours of each other. In another embodiment, two or more expression vectors are transfected into the host cells substantially simultaneously. For the purposes of the present disclosure, substantially simultaneously refers to any time period that is less than or equal to 1 hour.

Transformed cells are selected according to the selection markers present in the expression vector(s) to produce stable pools of transformed cells and then the pools are optionally cloned to yield stable clones. The stable clones produce between about 50 U/mL and about 300 U/mL, between about 50 U/mL and about 400 U/mL, between about 50 U/mL and about 350 U/mL, between about 50 U/mL and about 300 U/mL, between about 50 U/mL and about 250 U/mL, between about 50 U/mL and about 200 U/mL, between about 50 U/mL and about 175 U/mL, between about 50 U/mL and about 150 U/mL, between about 50 U/mL and about 125 U/mL, or between about 50 U/mL and about 100 U/mL of furin in the culture supernatant after about 36 to about 78 hours, about 36 to about 72 hours, about 40 hours to about 78 hours, about 42 hours to about 68 hours, or about 48 hours to about 72 hours after the initiation of the culture, or after culture for the indicated period of time. Furthermore, the stable clones yield more than 80% fully-processed and active recombinant mammalian protein, such as FX, of all the recombinant protein, such as FX, produced by the transformed cells.

Also disclosed herein is an expression system for recombinant furin and recombinant FX secreting furin into the culture supernatant at an accumulated concentration of between about 50 U/mL and about 300 U/mL after about 36 to about 78 hours of culture.

Also disclosed herein is a method of producing mature, fully-processed FX comprising use of an expression system secreting furin into the culture supernatant at an accumulated concentration between about 50 U/mL and about 300 U/mL after about 36 to about 78 hours of culture.

Also encompassed herein are recombinant mammalian proteins produced by the claimed methods and any full-processed mammalian recombinant FX.

EXAMPLES

Example 1

Production of Fully Processed and Fully Active Recombinant Factor X by Defined Levels of Furin For FX expression, the mammalian expression plasmid pSLX containing either human codon-optimized FX or both, human codon-optimized FX and human codon-optimized vitamin K epoxide reductase (FX/VKOR), separated by an internal ribosome entry site (IRES), was used. Constructs for Chinese hamster ovary (CHO)-S and CHO-DG44 expression systems included geneticin selection and dihydrofolate reductase (dhfr) selection, respectively. For furin expression, the mammalian expression plasmid pcDNA3.1 containing human full length furin in combination with hygromycin as selection marker was used (FIG. 1A).

Initially, CHO-derived cell lines (CHO-S and CHO DG44) were transfected with the FX or FX/VKOR constructs to generate stable pools and subsequently the pools were subjected to subcloning to generate stable clones. In a second round of transfection and subcloning, a selected number of FX- or FX/VKOR-expressing clones were each super-transfected with furin resulting in stable pools and stable clones expressing FX/furin or FX/VKOR/furin.

Stable recombinant FX-producing CHO-S and CHO-DG44 cell lines were grown in animal component-free media, in shaker flasks for about 42 to about 72 hours and with starting cell numbers of $0.3\times10^6$ or $0.5\times10^6$ cells/mL. CHO-S cells were maintained in PowerCHO®-CD media (Lonza BioWhittaker) supplemented with 4 mM glutamine, 500 μg/mL geneticin, 500 μg/mL hygromycin and 5 μg/mL vitamin K1. CHO-DG44 cells were maintained in OptiCHO™-CD media (Life Technologies) supplemented with 6 mM glutamine, 500 nM methotrexate (MTX) and 5 μg/mL vitamin K1.

The harvested cell culture supernatant was analyzed by Western blotting under reducing conditions to determine the quality of recombinant human FX using a polyclonal goat anti-human FX or polyclonal sheep anti-human FX (Affinity Biologicals). Densitometric analysis of the Western blots enabled the quantification of the different species of correctly processed FX, termed heavy chain FX (HC) and light chain FX (LC), and inadequately cleaved FX species, termed single chain FX (SC) and propeptide-containing light chain FX (PP-LC).

For FX quantification, the cell culture supernatant was analyzed with ELISA to determine the FX concentration and with the FXa chromogenic assay using Russell's viper venom (RVV) as activator to determine the concentration of active FX. These assays were calibrated using plasma-derived FX (Hyphen Biomed). The specific activity is given in %, by dividing the concentration of active FX by the concentration of total FX multiplied by 100. For furin quantification, active furin was determined in a furin fluorogenic assay calibrated against a furin reference material (New England Biolabs).

For statistical analysis, fully processed FX/total FX (%) was modeled as a function of furin concentration using the $E_{max}$ model on CHO-DG44 transfection pools (A), CHO-S transfection pools (B), and CHO-S single cell-derived clones (C). This model is used for statistical evaluation of dose-response studies. The $E_{max}$ model uses four parameters ($E_0$, $E_{max}$, $ED_{50}$, and n) to model FX as a function of furin as follows:

$$y=E_0+(x^n\cdot E_{max})/(ED^n{}_{50}=x^n)$$

where y refers to the fully-processed FX/total FX and x refers to the furin concentration. The parameter $E_0$ refers to the basal effect corresponding to the response when the furin concentration is zero, $E_{max}$ to the maximum effect attributable to the furin concentration, $ED_{50}$ to the furin concentration which produces half of $E_{max}$, and the parameter n represents the slope (Hill factor) determining the steepness of the curve.

To account that fully-processed FX/total FX approaches 100% if furin approaches an infinite large concentration, the $E_{max}$ model was modified to a function with three parameters to be estimated as follows;

$$y=E_0+(x^n\cdot(100-E_0)/(ED^n{}_{50}=x^n)$$

This model was fitted to the data taking the variability among the three different cell lines into account using a non-linear mixed effects model by allowing the parameters $E_0$ and n to vary between the different cell lines by also modeling these two parameters as random effects.

Model diagnostics was done to validate the applied model. A comparison of the fitted $E_{max}$ model with the null model using the likelihood ratio test was performed to determine statistical evidence for the $E_{max}$ model estimating the percentage of fully processed FX of total FX depending on the furin concentration.

Results

The CHO-based heterologous expression system for human FX, comprising CHO-DG44 transfection pools (A), CHO-S transfection pools (B), and CHO-S single cell-derived clones (C), was used as a basis to study the effect of furin expression on human FX processing following different transfection strategies. Transfection pools, as well as clones, additionally expressed VKOR which had no impact on the study.

Figure 4:
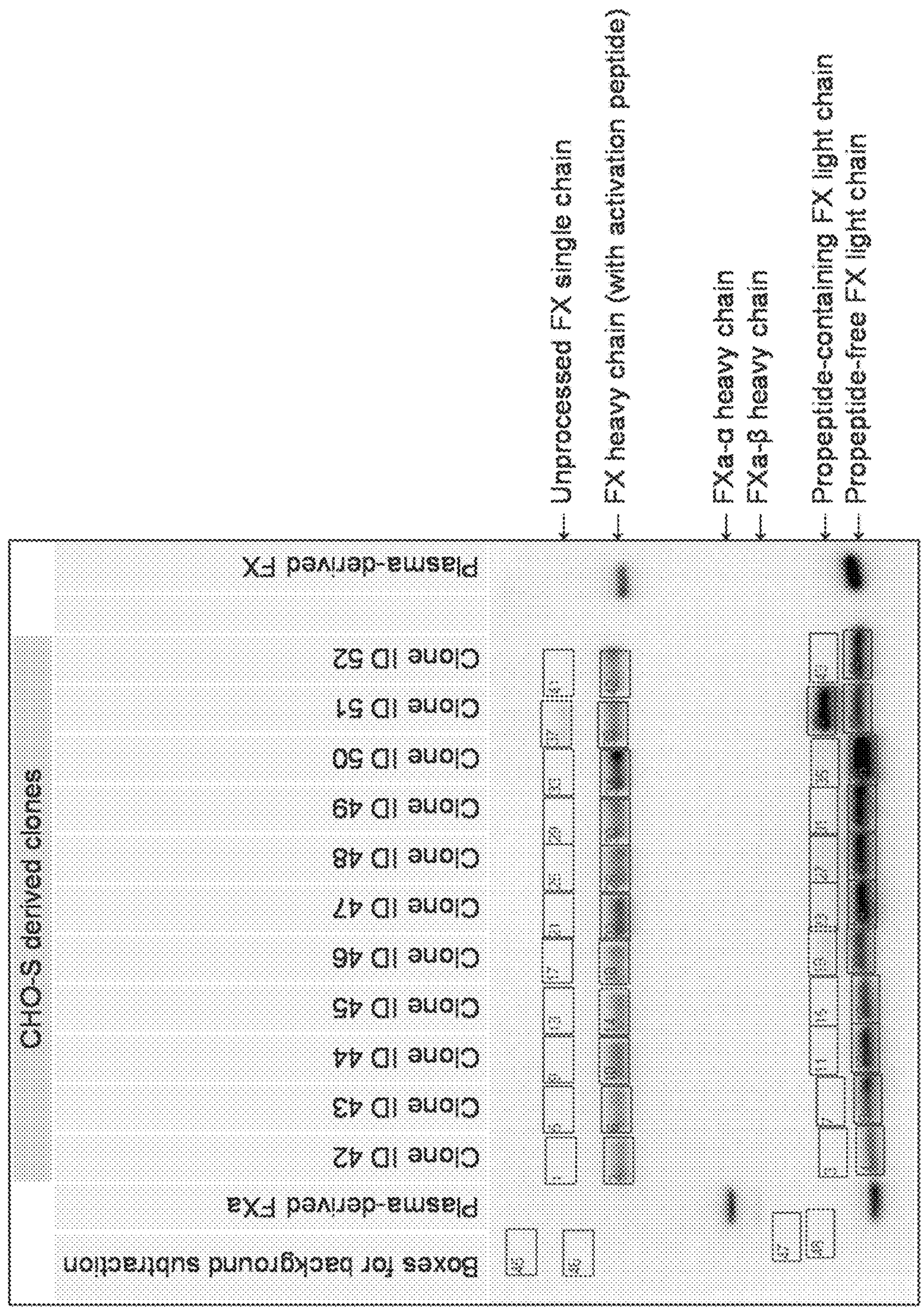
FIG. 4 depicts the degree of fully processed Factor X (FX) in cultures. Densitometric quantification was conducted of a FX Western blot under reducing conditions and stained with a polyclonal anti-FX antibody. The clones (clone ID 42 to 52) exhibit up to 4 species of FX with varying pixel intensities including the unprocessed FX single chain (box 1, 5, 9, etc.), the FX heavy chain (box 2, 6, 10, etc.), the unprocessed propeptide-containing FX light chain (box 3, 7, 11, etc.) and the processed FX light chain (box 4, 8, 12, etc.). The pixel intensity of boxes 45-48 was determined for background subtraction.
Figure 5:
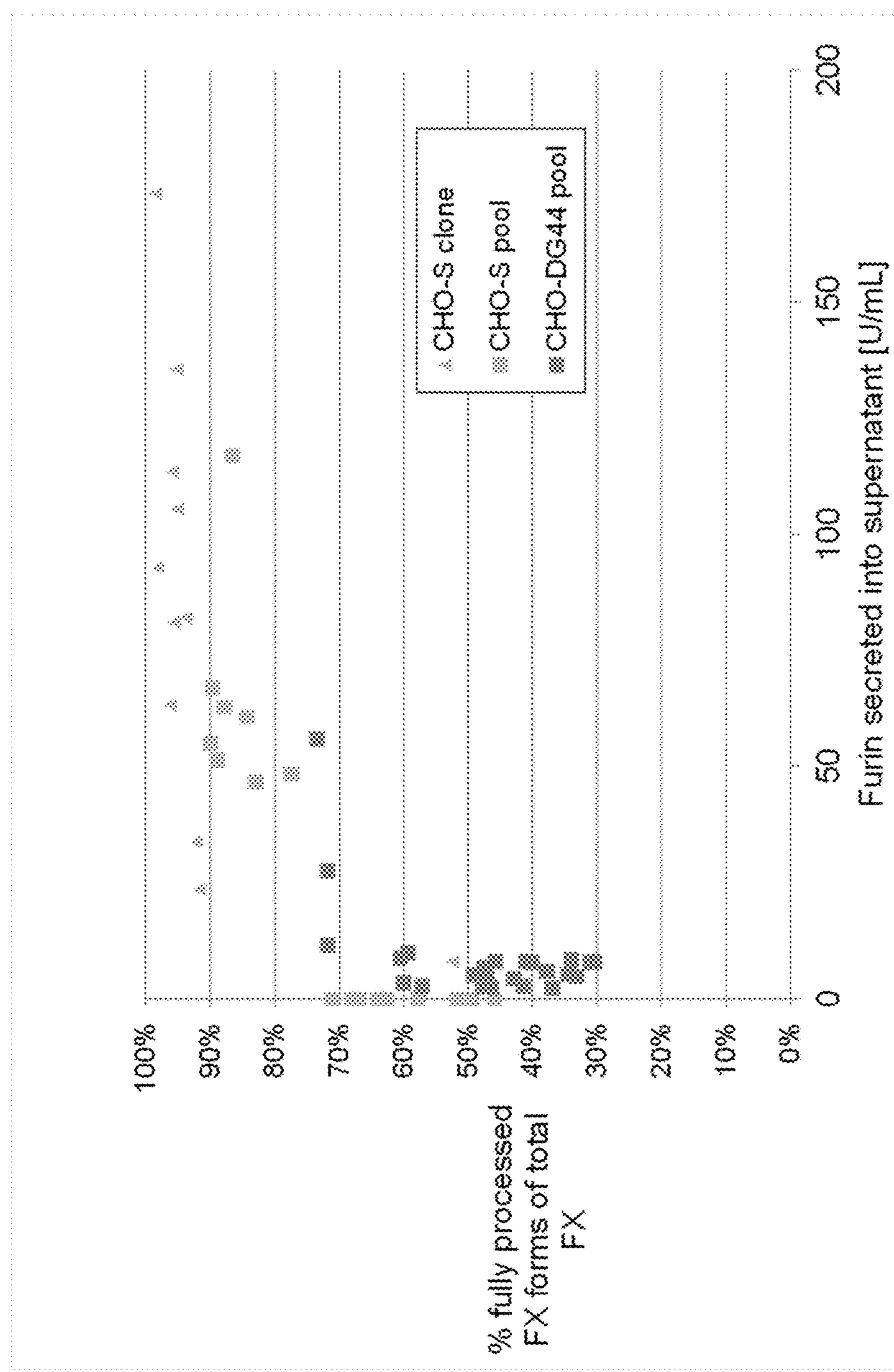
FIG. 5 depicts the secreted furin concentration and the percentage of fully processed FX/total FX in culture. A dose-response relationship exists between the secreted furin concentration in the cell culture supernatant (determined with a furin activity assay) and the % fully processed FX/total FX (determined by densitometric quantification of respective bands in Western blots).

After an incubation period of two to three culture days, the cell culture supernatant was subjected to a series of analyses, including Western blot analysis under reducing conditions, furin activity assay, ELISA and RVV assay (Table 1). On average, FX-producing CHO pools and clones revealed a FX specific activity of over 50%, partly reaching 100% (Table 1). Western blot analyses showed that the recombinant FX was inadequately processed to different degrees, as shown by two incompletely processed forms of FX (i.e. the propeptide-containing FX light chain and the FX single chain) besides the fully processed, propeptide-free FX light chain and FX heavy chain (FIG. 4). By means of densitrometric analysis of these four species of FX, the percentage of fully processed FX, i.e. FX light chain plus FX heavy chain in relation to total FX, ranged between 30% and almost 100% in cell culture supernatants (Table 1, FIG. 4). Furthermore, no pre-activation was observed, which would be visible as heavy chain band shortened by the size of the missing activation peptide. Also evaluated was whether the concentration of secreted furin had an influence on the degree of processed FX by plotting these two parameters (FIG. 5). As shown in FIG. 5, only partial processing of FX is feasible with low concentrations of secreted furin (<20 U/mL), whereas higher levels of secreted furin correlate with better processed FX.

Figure 6:
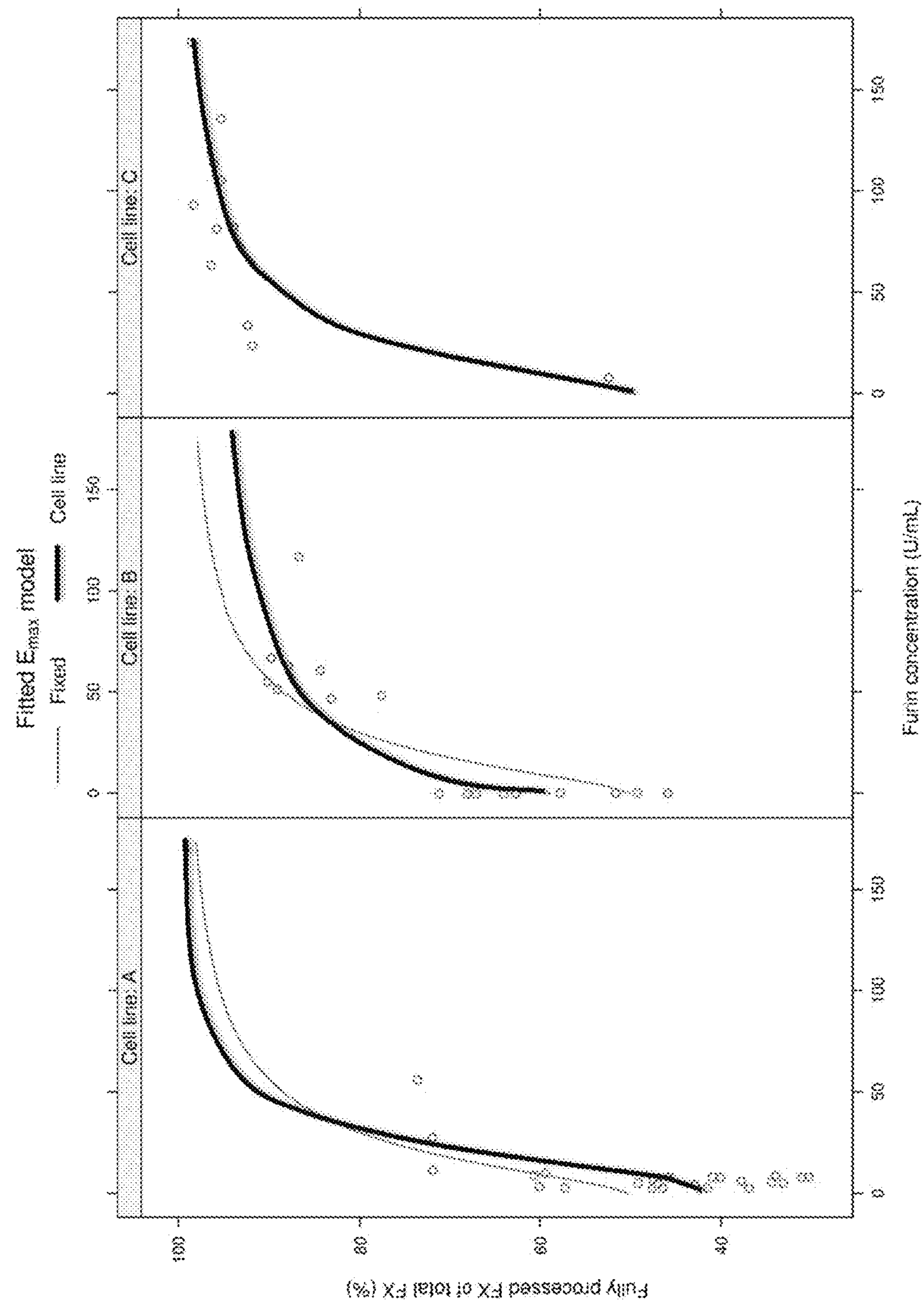
FIG. 6 depicts an analysis of furin dose and fully processed FX. Data (circles) with cell specific (dark lines) and population average (light lines) predicted fully processed FX/total FX (%) as a function of furin concentration with the $E_{max}$ model.
Figure 7A:
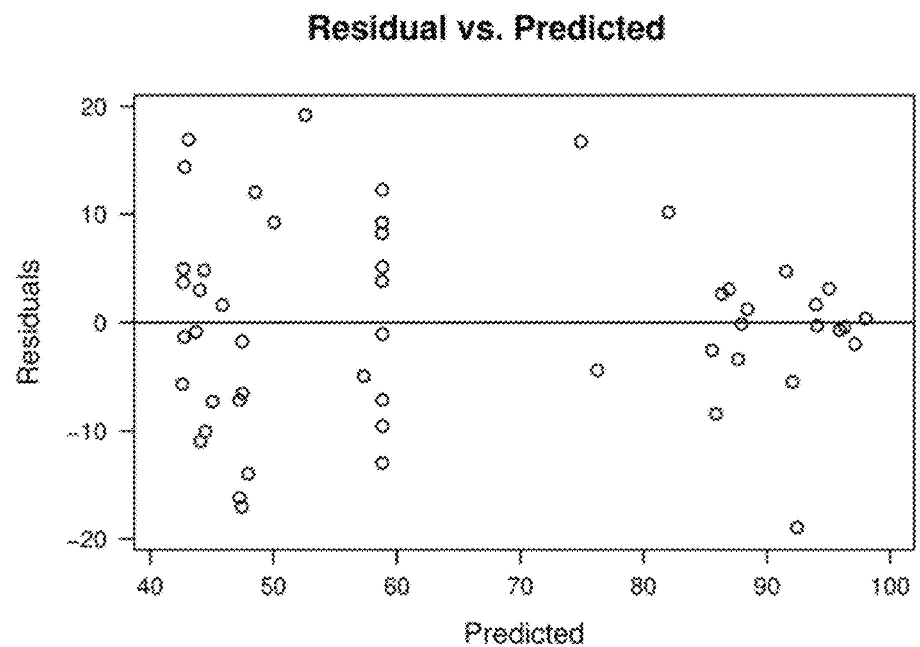
FIGS. 7A-D depict an $E_{max}$ model validity test.
Figure 7B:
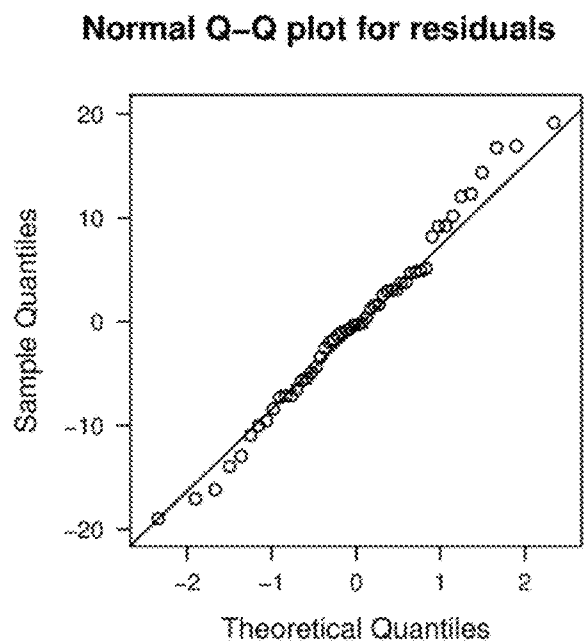
Figure 7C:
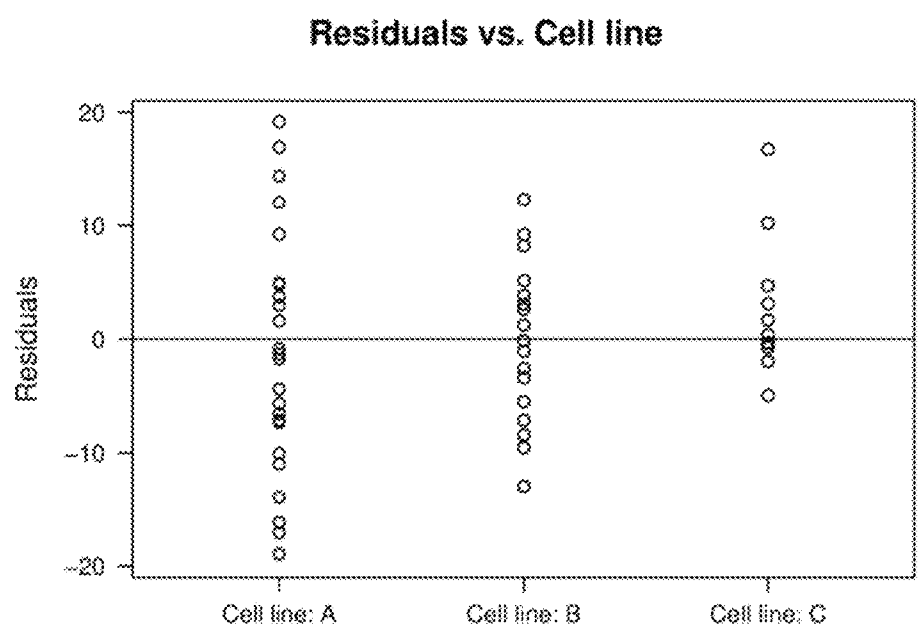
Figure 7D:
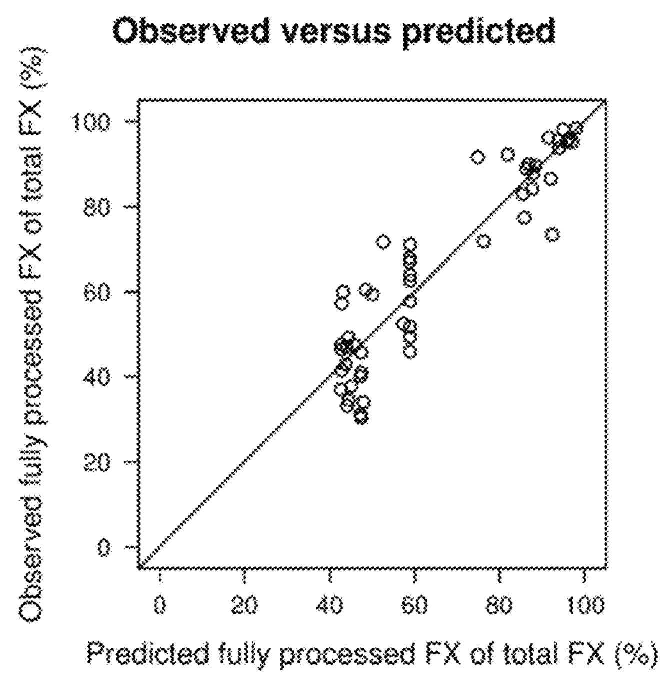
Figure 8:
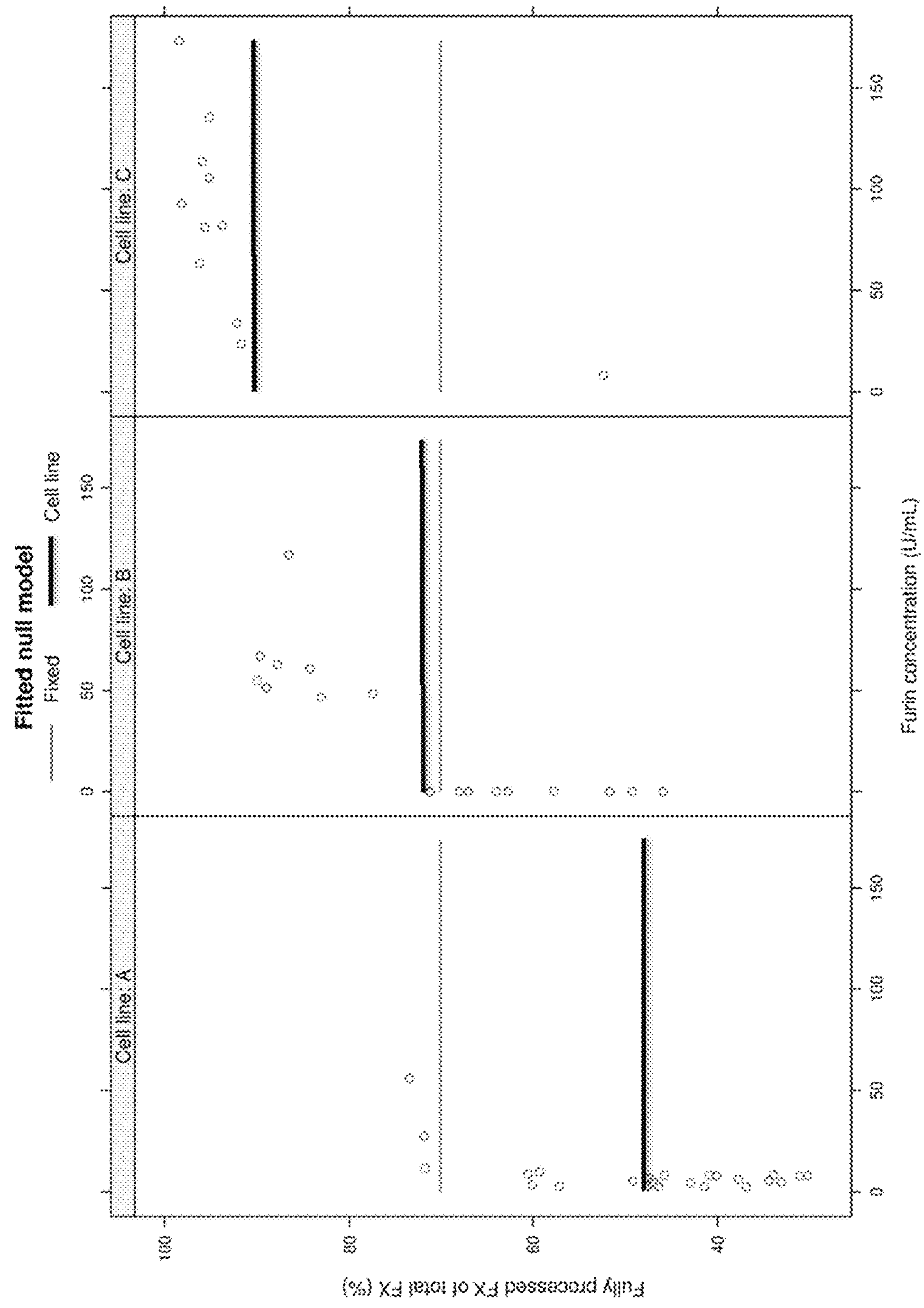
FIG. 8 depicts a null model for testing the hypothesis that the degree of FX processing is independent of furin concentration. Data (circles) and the fitted null model with intercepts only assuming that processed FX is independent from the furin concentration (cell specific and population averages fits as dark and light lines, respectively).
Figure 9:
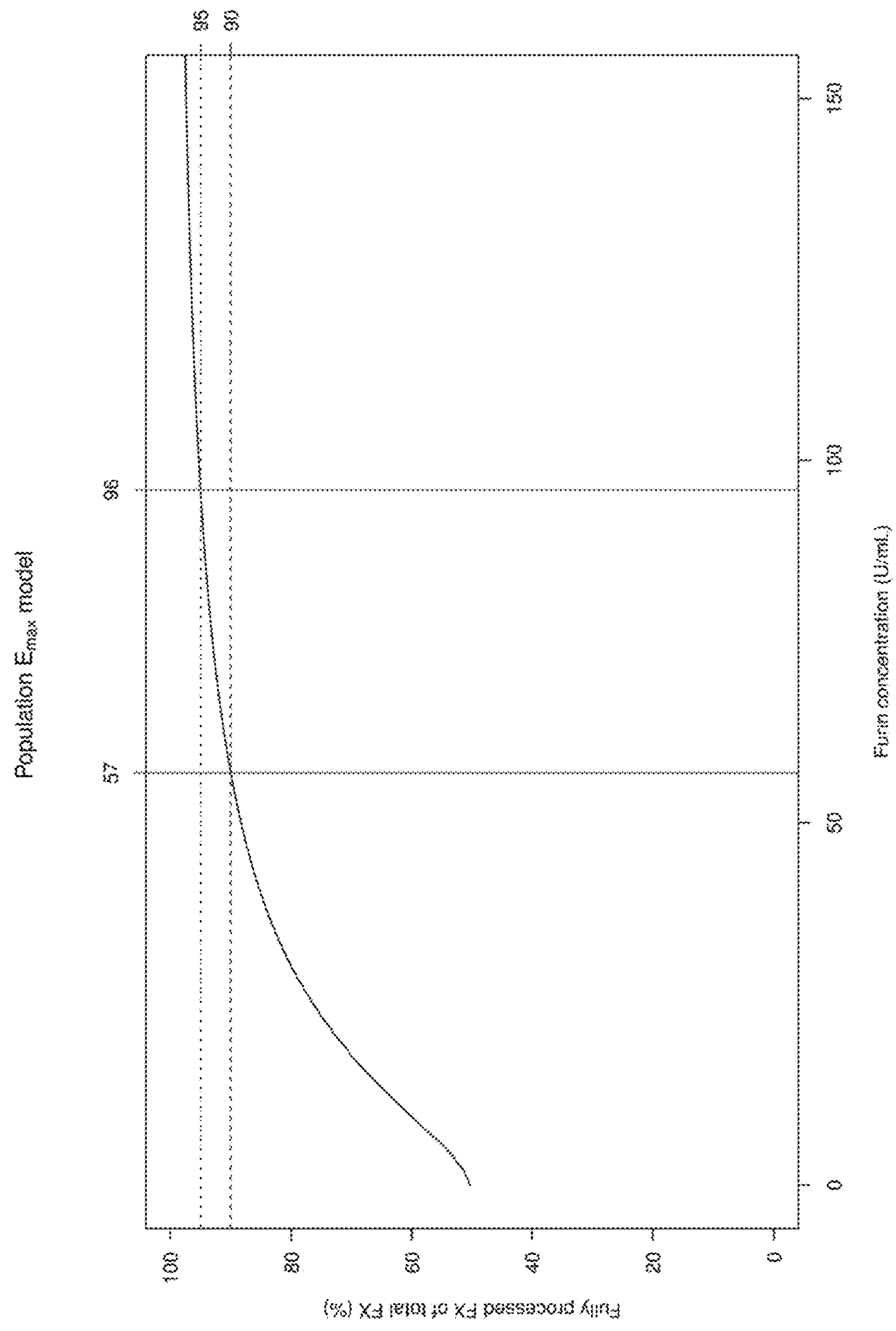
FIG. 9 depicts a dose-response curve and calculated furin minimum concentrations to yield 90% and 95% processed FX. The population average predicted of fully processed FX/total FX (%) as a function of furin concentration (black line) along with furin concentrations that give 90% and 95% fully processed FX/total FX obtained by numerical optimization of the fitted model.

To understand the influence of furin on FX processing and to provide statistical support of the data, fully processed FX of total FX (%) was modeled as a function of furin concentration using the $E_{max}$ model on cell lines A, B and C (FIG. 6). Four model diagnostics plots, indicating a good fit of the model to the data, are provided in FIGS. 7A-D. A comparison of the fitted $E_{max}$ model with the null model using the likelihood ratio test resulted in a p-value<0.0001, providing statistical evidence for a higher percentage of fully processed FX of total FX depending on a higher furin concentration (FIG. 8), once again proving validity of the data. Based on the statistical analysis, the estimated furin concentrations to be produced by the production cell line as detected in the cell culture medium together with FX resulting in equal or higher 90% and equal or higher 95% fully processed FX of total FX were at least 57 U/mL and at least 96 U/mL, respectively (FIG. 9).

In summary, the data provides a defined minimal level of secreted furin (at least 57 U/mL and at least 96 U/mL) in the cell culture supernatant that is required for sufficient FX processing (equal or higher 90% and equal or higher 95%).

In biotechnological processes that express high levels of recombinant protein, furin overexpression may be used to obtain fully processed zymogens. With our invention, we provide for the first time a defined minimum of secreted furin warranting for high FX processing (57 U/mL to achieve at least 90% fully processed FX and 96 U/mL furin for at least 95% fully processed FX). This finding is particularly beneficial to fermentation processes expressing recombinant FX, FXa and variants from human and animal species, where the furin level may be used as an indicator for adequate processing of the FX precursor protein, and as target for cell line and process development.

TABLE 1

Data summary of FX and furin co-expressing cell lines: shown are FX productivities, furin productivities and titers, and percentages of fully processed FX/total FX measured for each cell line.

| Clone/Pool ID | Expressed Recombinant Proteins | Cell line (pool or clone) | Furin conc. (U/mL) | Final cell density [$10^6$ cells/mL] | Furin Specific Productivity [U/$10^6$ cells/day] | FX specific activity [%] | Fully processed FX/total FX (%) |
|---|---|---|---|---|---|---|---|
| 1 | FX | CHO-DG44 pool | 8.03 | 2.015 | 2.22 | 5.64 | 30.34 |
| 2 | FX/Furin | CHO-DG44 pool | 8.05 | 1.155 | 3.45 | 7.58 | 45.69 |
| 3 | FX/VKOR | CHO-DG44 pool | 7.88 | 1.436 | 2.86 | 6.44 | 31.05 |
| 4 | FX/VKOR/Furin | CHO-DG44 pool | 7.88 | 1.029 | 3.68 | 11.16 | 40.08 |
| 5 | FX | CHO-DG44 pool | 2.74 | 1.518 | 0.95 | 9.04 | 41.42 |
| 6 | FX/Furin | CHO-DG44 pool | 11.59 | 0.952 | 5.71 | 14.12 | 71.78 |
| 7 | FX/VKOR | CHO-DG44 pool | 2.38 | 1.152 | 1.02 | 15.14 | 36.92 |
| 8 | FX/VKOR/Furin | CHO-DG44 pool | 2.82 | 0.795 | 1.58 | 29.37 | 57.17 |
| 9 | FX | CHO-DG44 pool | 5.36 | 2.438 | 1.26 | 9.23 | 34.46 |
| 10 | FX/Furin | CHO-DG44 pool | 9.94 | 1.503 | 3.48 | 12.23 | 59.30 |
| 11 | FX/VKOR | CHO-DG44 pool | 4.88 | 2.162 | 1.27 | 14.57 | 33.12 |
| 12 | FX/VKOR/Furin | CHO-DG44 pool | 4.78 | 1.372 | 1.80 | 20.48 | 46.98 |
| 13 | FX | CHO-DG44 pool | 8.07 | 2.005 | 2.24 | 47.68 | 40.93 |
| 14 | FX/Furin | CHO-DG44 pool | 8.83 | 1.851 | 2.62 | 64.80 | 60.54 |
| 15 | FX/VKOR | CHO-DG44 pool | 8.42 | 1.843 | 2.50 | 45.48 | 33.98 |
| 16 | FX/VKOR/Furin | CHO-DG44 pool | 6.72 | 2.220 | 1.71 | 58.04 | 47.46 |
| 17 | FX | CHO-DG44 pool | 2.59 | 1.246 | 1.05 | 78.72 | 46.40 |
| 18 | FX/Furin | CHO-DG44 pool | 55.91 | 1.396 | 20.75 | 98.49 | 73.47 |
| 19 | FX/VKOR | CHO-DG44 pool | 2.59 | 1.207 | 1.07 | 70.43 | 47.61 |
| 20 | FX/VKOR/Furin | CHO-DG44 pool | 3.48 | 1.431 | 1.27 | 93.42 | 60.04 |
| 21 | FX | CHO-DG44 pool | 5.96 | 2.035 | 1.63 | 71.19 | 37.77 |
| 22 | FX/Furin | CHO-DG44 pool | 27.57 | 2.226 | 7.00 | 104.40 | 71.85 |
| 23 | FX/VKOR | CHO-DG44 pool | 4.40 | 1.827 | 1.32 | 69.50 | 42.84 |
| 24 | FX/VKOR/Furin | CHO-DG44 pool | 5.20 | 2.283 | 1.29 | 75.60 | 49.19 |
| 25 | FX/VKOR | CHO-S pool | 0.00 | 2.224 | 0.00 | 90.59 | 63.96 |
| 26 | FX/VKOR/Furin | CHO-S pool | 51.34 | 1.828 | 25.20 | 99.57 | 88.97 |
| 27 | FX/VKOR | CHO-S pool | 0.00 | 2.851 | 0.00 | 49.99 | 57.75 |
| 28 | FX/VKOR/Furin | CHO-S pool | 62.84 | 2.248 | 26.13 | 48.73 | 87.78 |
| 29 | FX/VKOR | CHO-S pool | 0.00 | 3.584 | 0.00 | 81.39 | 68.02 |
| 30 | FX/VKOR/Furin | CHO-S pool | 66.98 | 2.362 | 26.75 | 66.57 | 89.64 |
| 31 | FX/VKOR | CHO-S pool | 0.00 | 2.870 | 0.00 | 69.04 | 67.02 |
| 32 | FX/VKOR/Furin | CHO-S pool | 55.08 | 2.295 | 22.52 | 52.91 | 89.99 |
| 33 | FX/VKOR | CHO-S pool | 0.00 | 2.645 | 0.00 | 59.62 | 71.13 |
| 34 | FX/Furin | CHO-S pool | 116.89 | 2.083 | 50.52 | 51.40 | 86.56 |
| 35 | FX | CHO-S pool | 0.00 | 2.230 | 0.00 | 67.49 | 62.65 |
| 36 | FX/Furin | CHO-S pool | 46.62 | 1.846 | 22.18 | 19.29 | 82.99 |
| 37 | FX | CHO-S pool | 0.00 | 2.049 | 0.00 | 11.47 | 51.69 |
| 38 | FX/Furin | CHO-S pool | 48.41 | 1.457 | 27.61 | <25.33 | 77.46 |
| 39 | FX | CHO-S pool | 0.00 | 2.265 | 0.00 | 95.04 | 45.87 |
| 40 | FX/Furin | CHO-S pool | 60.72 | 1.566 | 32.80 | 27.69 | 84.27 |
| 41 | FX | CHO-S pool | 0.00 | 2.018 | 0.00 | 35.63 | 49.28 |
| 42 | FX/VKOR/Furin | CHO-S clone | 113.45 | 3.704 | 26.99 | 90.30 | 95.91 |
| 43 | FX/VKOR/Furin | CHO-S clone | 63.41 | 3.133 | 17.45 | 92.26 | 96.23 |
| 44 | FX/VKOR/Furin | CHO-S clone | 92.86 | 2.893 | 27.37 | 98.55 | 98.12 |
| 45 | FX/VKOR/Furin | CHO-S clone | 173.37 | 3.430 | 44.11 | 79.46 | 98.42 |

TABLE 1-continued

Data summary of FX and furin co-expressing cell lines: shown are FX productivities, furin productivities and titers, and percentages of fully processed FX/total FX measured for each cell line.

| Clone/ Pool ID | Expressed Recombinant Proteins | Cell line (pool or clone) | Furin conc. (U/mL) | Final cell density [$10^6$ cells/mL] | Furin Specific Productivity [U/$10^6$ cells/day] | FX specific activity [%] | Fully processed FX/total FX (%) |
|---|---|---|---|---|---|---|---|
| 46 | FX/VKOR/Furin | CHO-S clone | 23.54 | 2.816 | 7.10 | 86.31 | 91.69 |
| 47 | FX/VKOR/Furin | CHO-S clone | 105.42 | 2.918 | 30.84 | 78.63 | 95.14 |
| 48 | FX/VKOR/Furin | CHO-S clone | 33.77 | 3.542 | 8.35 | 80.02 | 92.21 |
| 49 | FX/VKOR/Furin | CHO-S clone | 135.62 | 2.777 | 41.39 | 94.46 | 95.18 |
| 50 | FX/VKOR/Furin | CHO-S clone | 82.03 | 2.193 | 30.46 | 48.80 | 93.75 |
| 51 | FX/VKOR/Furin | CHO-S clone | 8.06 | 2.280 | 2.90 | 67.11 | 52.38 |
| 52 | FX/VKOR/Furin | CHO-S clone | 81.02 | 2.889 | 23.91 | 85.37 | 95.61 |

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An isolated eukaryotic transformed cell comprising:

a first exogenous nucleic acid encoding a human furin and a second exogenous nucleic acid encoding a human Factor X, such that the transformed cell expresses and secretes the human furin and the human Factor X into a culture supernatant, wherein the human furin is secreted at a concentration of about 60 U/mL to about 300 U/mL in the culture supernatant after culture for about 36 to about 78 hours and at least 85% of the human Factor X is fully processed, and wherein the first exogenous nucleic acid and the second exogenous nucleic acid are present on one or two plasmids.

2. The isolated eukaryotic transformed cell of claim 1, wherein the plasmid(s) is a non-viral expression vector.

3. The isolated eukaryotic transformed cell of claim 1, wherein the plasmid(s) is a viral expression vector.

4. The isolated eukaryotic transformed cell of claim 1, wherein the human furin is secreted at a concentration of about 100 to about 300 U/mL in the culture supernatant after culture for about 36 to about 78 hours.

5. The isolated eukaryotic transformed cell of claim 4, wherein at least 90% of the human Factor X produced by the transformed cell is fully processed.

6. The isolated eukaryotic transformed cell of claim 1, wherein the human furin is secreted at a concentration of at least about 90 to about 100 U/mL in the culture supernatant after culture for about 36 to about 78 hours.

7. The isolated eukaryotic transformed cell of claim 6, wherein at least 95% of the human Factor X produced by the transformed cell is fully processed.

8. The isolated eukaryotic transformed cell of claim 1, wherein the human furin concentration in the culture supernatant reaches about 60 to about 300 U/mL after culture for about 42 to about 72 hours.

9. The isolated eukaryotic transformed cell of claim 1, wherein the cell is selected from the group consisting of a Chinese hamster ovary (CHO) cell, a human embryonic kidney cell, a primate kidney cell, a fibroblast, and a mouse myeloma cells.

10. The isolated eukaryotic transformed cell of claim 1, further comprising an exogenous nucleic acid encoding a human vitamin K epoxide reductase (VKOR).

11. An isolated eukaryotic transformed cell comprising:

a first expression vector comprising an exogenous nucleic acid encoding a human furin; wherein the transformed cell secretes the human furin into the culture supernatant at a concentration of about 60 U/mL to about 300 U/mL after culture for about 36 to about 78 hours, and wherein the first expression vector is a plasmid.

12. The isolated eukaryotic transformed cell of claim 11, wherein the cell is selected from the group consisting of a Chinese hamster ovary (CHO) cell, a human embryonic kidney cell, a primate kidney cell, a fibroblast, and a mouse myeloma cells.

13. The isolated eukaryotic transformed cell of claim 11, further comprising an exogenous nucleic acid encoding a human vitamin K epoxide reductase (VKOR).

14. The isolated eukaryotic transformed cell of claim 11, wherein the transformed cell further comprises an exogenous nucleic acid encoding a protein, and wherein the protein comprises an Arg-(Lys/Arg)-Arg motif and is cleavable by the human furin.

15. The isolated eukaryotic transformed cell of claim 14, wherein the protein is von Willebrand Factor, Factor II, Factor IX, Factor X, Protein C, Protein S, or Protein Z.

16. The isolated eukaryotic transformed cell of claim 14, wherein the exogenous nucleic acid encoding the protein is on a second expression vector.

* * * * *

SEQUENCE LISTING

<160> NUMBER OF SEQ ID NOS: 4

<210> SEQ ID NO 1
<211> LENGTH: 7981
<212> TYPE: DNA
<213> ORGANISM: Artificial Sequence
<220> FEATURE:
<223> OTHER INFORMATION: RCL.012-74.pD3H-Furin expression vector

<400> SEQUENCE: 1

```
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattctgc    960
agatatccag cacagtggcg gccgcatgga gctgaggccc tggttgctat gggtggtagc   1020
agcaacagga accttggtcc tgctagcagc tgatgctcag ggccagaagg tcttcaccaa   1080
cacgtgggct gtgcgcatcc ctggaggccc agcggtggcc aacagtgtgg cacggaagca   1140
tgggttcctc aacctgggcc agatcttcgg ggactattac cacttctggc atcgaggagt   1200
gacgaagcgg tccctgtcgc ctcaccgccc gcggcacagc cggctgcaga gggagcctca   1260
agtacagtgg ctggaacagc aggtggcaaa gcgacggact aaacgggacg tgtaccagga   1320
gcccacagac cccaagtttc ctcagcagtg gtacctgtct ggtgtcactc agcgggacct   1380
gaatgtgaag gcggcctggg cgcagggcta cacagggcac ggcattgtgg tctccattct   1440
ggacgatggc atcgagaaga accacccgga cttggcaggc aattatgatc ctggggccag   1500
ttttgatgtc aatgaccagg accctgaccc ccagcctcgg tacacacaga tgaatgacaa   1560
caggcacggc acacggtgtg cgggggaagt ggctgcggtg gccaacaacg gtgtctgtgg   1620
tgtaggtgtg gcctacaacg cccgcattgg aggggtgcgc atgctggatg gcgaggtgac   1680
agatgcagtg gaggcacgct cgctgggcct gaaccccaac cacatccaca tctacagtgc   1740
cagctggggc cccgaggatg acggcaagac agtggatggg ccagcccgcc tcgccgagga   1800
ggccttcttc cgtggggtta gccagggccg agggggggctg ggctccatct ttgtctgggc   1860
ctcggggaac gggggccggg aacatgacag ctgcaactgc gacggctaca ccaacagtat   1920
ctacacgctg tccatcagca gcgccacgca gtttggcaac gtgccgtggt acagcgaggc   1980
ctgctcgtcc acactggcca cgacctacag cagtggcaac cagaatgaga agcagatcgt   2040
```

-continued

```
gacgactgac ttgcggcaga agtgcacgga gtctcacacg ggcacctcag cctctgcccc   2100
cttagcagcc ggcatcattg ctctcaccct ggaggccaat aagaacctca catggcggga   2160
catgcaacac ctggtggtac agacctcgaa gccagcccac ctcaatgcca acgactgggc   2220
caccaatggt gtgggccgga aagtgagcca ctcatatggc tacgggcttt tggacgcagg   2280
cgccatggtg gccctggccc agaattggac cacagtggcc ccccagcgga agtgcatcat   2340
cgacatcctc accgagccca aagacatcgg gaaacggctc gaggtgcgga agaccgtgac   2400
cgcgtgcctg ggcgagccca accacatcac tcggctggag cacgctcagg cgcggctcac   2460
cctgtcctat aatcgccgtg gcgacctggc catccacctg gtcagcccca tgggcacccg   2520
ctccaccctg ctggcagcca ggccacatga ctactccgca gatgggttta atgactgggc   2580
cttcatgaca actcattcct gggatgagga tccctctggc gagtgggtcc tagagattga   2640
aaacaccagc gaagccaaca actatgggac gctgaccaag ttcaccctcg tactctatgg   2700
caccgcccct gaggggctgc ccgtacctcc agaaagcagt ggctgcaaga ccctcacgtc   2760
cagtcaggcc tgtgtggtgt gcgaggaagg cttctccctg caccagaaga gctgtgtcca   2820
gcactgccct ccaggcttcg ccccccaagt cctcgatacg cactatagca ccgagaatga   2880
cgtggagacc atccgggcca gcgtctgcgc cccctgccac gcctcatgtg ccacatgcca   2940
ggggccggcc ctgacagact gcctcagctg ccccagccac gcctccttgg accctgtgga   3000
gcagacttgc tcccggcaaa gccagagcag ccgagagtcc ccgccacagc agcagccacc   3060
tcggctgccc ccggaggtgg aggcggggca acggctgcgg gcagggctgc tgccctcaca   3120
cctgcctgag gtggtggccg gcctcagctg cgccttcatc gtgctggtct tcgtcactgt   3180
cttcctggtc ctgcagctgc gctctggctt tagttttcgg ggggtgaagg tgtacaccat   3240
ggaccgtggc ctcatctcct acaaggggct gccccctgaa gcctggcagg aggagtgccc   3300
gtctgactca gaagaggacg agggccgggg cgagaggacc gcctttatca aagaccagag   3360
cgccctctga tctagagggc ccgtttaaac ccgctgatca gcctcgactg tgccttctag   3420
ttgccagcca tctgttgttt gcccctcccc cgtgccttcc ttgaccctgg aaggtgccac   3480
tcccactgtc ctttcctaat aaaatgagga aattgcatcg cattgtctga gtaggtgtca   3540
ttctattctg gggggtgggg tggggcagga cagcaagggg gaggattggg aagacaatag   3600
caggcatgct ggggatgcgg tgggctctat ggcttctgag gcggaaagaa ccagctgggg   3660
ctctaggggg tatccccacg cgccctgtag cggcgcatta agcgcggcgg gtgtggtggt   3720
tacgcgcagc gtgaccgcta cacttgccag cgccctagcg cccgctcctt tcgctttctt   3780
cccttccttt ctcgccacgt tcgccggctt tccccgtcaa gctctaaatc ggggcatccc   3840
tttagggttc cgatttagtg ctttacggca cctcgacccc aaaaaacttg attagggtga   3900
tggttcacgt agtgggccat cgccctgata gacggttttt cgccctttga cgttggagtc   3960
cacgttcttt aatagtggac tcttgttcca aactggaaca acactcaacc ctatctcggt   4020
ctattctttt gatttataag ggattttggg gatttcggcc tattggttaa aaaatgagct   4080
gatttaacaa aaatttaacg cgaattaatt ctgtggaatg tgtgtcagtt agggtgtgga   4140
aagtccccag gctccccagg caggcagaag tatgcaaagc atgcatctca attagtcagc   4200
aaccaggtgt ggaaagtccc caggctcccc agcaggcaga agtatgcaaa gcatgcatct   4260
caattagtca gcaaccatag tcccgcccct aactccgccc atcccgcccc taactccgcc   4320
cagttccgcc cattctccgc cccatggctg actaattttt tttatttatg cagaggccga   4380
```

```
ggccgcctct gcctctgagc tattccagaa gtagtgagga ggcttttttg gaggcctagg   4440
cttttgcaaa aagctcccgg gagcttgtat atccattttc ggatctgatc agcacgtgat   4500
gaaaaagcct gaactcaccg cgacgtctgt cgagaagttt ctgatcgaaa agttcgacag   4560
cgtctccgac ctgatgcagc tctcggaggg cgaagaatct cgtgctttca gcttcgatgt   4620
aggagggcgt ggatatgtcc tgcgggtaaa tagctgcgcc gatggtttct acaaagatcg   4680
ttatgtttat cggcactttg catcggccgc gctcccgatt ccggaagtgc ttgacattgg   4740
ggaattcagc gagagcctga cctattgcat ctcccgccgt gcacagggtg tcacgttgca   4800
agacctgcct gaaaccgaac tgcccgctgt tctgcagccg gtcgcggagg ccatggatgc   4860
gatcgctgcg gccgatctta gccagacgag cgggttcggc ccattcggac cgcaaggaat   4920
cggtcaatac actacatggc gtgatttcat atgcgcgatt gctgatcccc atgtgtatca   4980
ctggcaaact gtgatggacg acaccgtcag tgcgtccgtc gcgcaggctc tcgatgagct   5040
gatgctttgg gccgaggact gccccgaagt ccggcacctc gtgcacgcgg atttcggctc   5100
caacaatgtc ctgacggaca atggccgcat aacagcggtc attgactgga gcgaggcgat   5160
gttcggggat tcccaatacg aggtcgccaa catcttcttc tggaggccgt ggttggcttg   5220
tatggagcag cagacgcgct acttcgagcg gaggcatccg gagcttgcag gatcgccgcg   5280
gctccgggcg tatatgctcc gcattggtct tgaccaactc tatcagagct tggttgacgg   5340
caatttcgat gatgcagctt gggcgcaggg tcgatgcgac gcaatcgtcc gatccggagc   5400
cgggactgtc gggcgtacac aaatcgcccg cagaagcgcg gccgtctgga ccgatggctg   5460
tgtagaagta ctcgccgata gtggaaaccg acgccccagc actcgtccga gggcaaagga   5520
atagcacgtg ctacgagatt tcgattccac cgccgccttc tatgaaaggt tgggcttcgg   5580
aatcgttttc cgggacgccg gctggatgat cctccagcgc ggggatctca tgctggagtt   5640
cttcgcccac cccaacttgt ttattgcagc ttataatggt tacaaataaa gcaatagcat   5700
cacaaatttc acaaataaag catttttttc actgcattct agttgtggtt tgtccaaact   5760
catcaatgta tcttatcatg tctgtatacc gtcgacctct agctagagct tggcgtaatc   5820
atggtcatag ctgtttcctg tgtgaaattg ttatccgctc acaattccac acaacatacg   5880
agccggaagc ataaagtgta aagcctgggg tgcctaatga gtgagctaac tcacattaat   5940
tgcgttgcgc tcactgcccg ctttccagtc gggaaacctg tcgtgccagc tgcattaatg   6000
aatcggccaa cgcgcgggga gaggcggttt gcgtattggg cgctcttccg cttcctcgct   6060
cactgactcg ctgcgctcgg tcgttcggct gcggcgagcg gtatcagctc actcaaaggc   6120
ggtaatacgg ttatccacag aatcagggga taacgcagga aagaacatgt gagcaaaagg   6180
ccagcaaaag gccaggaacc gtaaaaaggc cgcgttgctg gcgtttttcc ataggctccg   6240
cccccctgac gagcatcaca aaaatcgacg ctcaagtcag aggtggcgaa acccgacagg   6300
actataaaga taccaggcgt ttccccctgg aagctccctc gtgcgctctc ctgttccgac   6360
cctgccgctt accggatacc tgtccgcctt tctcccttcg ggaagcgtgg cgctttctca   6420
atgctcacgc tgtaggtatc tcagttcggt gtaggtcgtt cgctccaagc tgggctgtgt   6480
gcacgaaccc cccgttcagc ccgaccgctg cgccttatcc ggtaactatc gtcttgagtc   6540
caacccggta agacacgact tatcgccact ggcagcagcc actggtaaca ggattagcag   6600
agcgaggtat gtaggcggtg ctacagagtt cttgaagtgg tggcctaact acggctacac   6660
tagaaggaca gtatttggta tctgcgctct gctgaagcca gttaccttcg gaaaaagagt   6720
tggtagctct tgatccggca aacaaaccac cgctggtagc ggtggttttt ttgtttgcaa   6780
```

```
gcagcagatt acgcgcagaa aaaaaggatc tcaagaagat cctttgatct tttctacggg   6840

gtctgacgct cagtggaacg aaaactcacg ttaagggatt ttggtcatga gattatcaaa   6900

aaggatcttc acctagatcc ttttaaatta aaaatgaagt tttaaatcaa tctaaagtat   6960

atatgagtaa acttggtctg acagttacca atgcttaatc agtgaggcac ctatctcagc   7020

gatctgtcta tttcgttcat ccatagttgc ctgactcccc gtcgtgtaga taactacgat   7080

acgggagggc ttaccatctg gccccagtgc tgcaatgata ccgcgagacc cacgctcacc   7140

ggctccagat ttatcagcaa taaaccagcc agccggaagg gccgagcgca gaagtggtcc   7200

tgcaacttta tccgcctcca tccagtctat taattgttgc cgggaagcta gagtaagtag   7260

ttcgccagtt aatagtttgc gcaacgttgt tgccattgct acaggcatcg tggtgtcacg   7320

ctcgtcgttt ggtatggctt cattcagctc cggttcccaa cgatcaaggc gagttacatg   7380

atcccccatg ttgtgcaaaa aagcggttag ctccttcggt cctccgatcg ttgtcagaag   7440

taagttggcc gcagtgttat cactcatggt tatggcagca ctgcataatt ctcttactgt   7500

catgccatcc gtaagatgct tttctgtgac tggtgagtac tcaaccaagt cattctgaga   7560

atagtgtatg cggcgaccga gttgctcttg cccggcgtca atacgggata ataccgcgcc   7620

acatagcaga actttaaaag tgctcatcat tggaaaacgt tcttcggggc gaaaactctc   7680

aaggatctta ccgctgttga gatccagttc gatgtaaccc actcgtgcac ccaactgatc   7740

ttcagcatct tttactttca ccagcgtttc tgggtgagca aaaacaggaa ggcaaaatgc   7800

cgcaaaaaag ggaataaggg cgacacggaa atgttgaata ctcatactct tcctttttca   7860

atattattga agcatttatc agggttattg tctcatgagc ggatacatat ttgaatgtat   7920

ttagaaaaat aaacaaatag gggttccgcg cacatttccc cgaaaagtgc cacctgacgt   7980

c                                                                   7981
```

```
<210> SEQ ID NO 2
<211> LENGTH: 2385
<212> TYPE: DNA
<213> ORGANISM: Homo sapiens

<400> SEQUENCE: 2

atggagctga ggccctggtt gctatgggtg gtagcagcaa caggaacctt ggtcctgcta     60

gcagctgatg ctcagggcca gaaggtcttc accaacacgt gggctgtgcg catccctgga    120

ggcccagcgg tggccaacag tgtggcacgg aagcatgggt tcctcaacct gggccagatc    180

ttcggggact attaccactt ctggcatcga ggagtgacga agcggtccct gtcgcctcac    240

cgcccgcggc acagccggct gcagagggag cctcaagtac agtggctgga acagcaggtg    300

gcaaagcgac ggactaaacg ggacgtgtac caggagccca cagaccccaa gtttcctcag    360

cagtggtacc tgtctggtgt cactcagcgg gacctgaatg tgaaggcggc ctgggcgcag    420

ggctacacag ggcacggcat tgtggtctcc attctggacg atggcatcga gaagaaccac    480

ccggacttgg caggcaatta tgatcctggg gccagttttg atgtcaatga ccaggaccct    540

gacccccagc ctcggtacac acagatgaat gacaacaggc acggcacacg gtgtgcgggg    600

gaagtggctg cggtggccaa caacggtgtc tgtggtgtag gtgtggccta caacgcccgc    660

attggagggg tgcgcatgct ggatggcgag gtgacagatg cagtggaggc acgctcgctg    720

ggcctgaacc ccaaccacat ccacatctac agtgccagct ggggccccga ggatgacggc    780

aagacagtgg atgggccagc ccgcctcgcc gaggaggcct tcttccgtgg ggttagccag    840
```

```
ggccgagggg ggctgggctc catctttgtc tgggcctcgg ggaacggggg ccgggaacat     900

gacagctgca actgcgacgg ctacaccaac agtatctaca cgctgtccat cagcagcgcc     960

acgcagtttg gcaacgtgcc gtggtacagc gaggcctgct cgtccacact ggccacgacc    1020

tacagcagtg gcaaccagaa tgagaagcag atcgtgacga ctgacttgcg gcagaagtgc    1080

acggagtctc acacgggcac ctcagcctct gccccttag cagccggcat cattgctctc     1140

accctggagg ccaataagaa cctcacatgg cgggacatgc aacacctggt ggtacagacc    1200

tcgaagccag cccacctcaa tgccaacgac tgggccacca atggtgtggg ccggaaagtg    1260

agccactcat atggctacgg gcttttggac gcaggcgcca tggtggccct ggcccagaat    1320

tggaccacag tggcccccca gcggaagtgc atcatcgaca tcctcaccga gcccaaagac    1380

atcgggaaac ggctcgaggt gcggaagacc gtgaccgcgt gcctgggcga gcccaaccac    1440

atcactcggc tggagcacgc tcaggcgcgg ctcaccctgt cctataatcg ccgtggcgac    1500

ctggccatcc acctggtcag ccccatgggc acccgctcca ccctgctggc agccaggcca    1560

catgactact ccgcagatgg gtttaatgac tgggccttca tgacaactca ttcctgggat    1620

gaggatccct ctggcgagtg ggtcctagag attgaaaaca ccagcgaagc caacaactat    1680

gggacgctga ccaagttcac cctcgtactc tatggcaccg cccctgaggg gctgcccgta    1740

cctccagaaa gcagtggctg caagaccctc acgtccagtc aggcctgtgt ggtgtgcgag    1800

gaaggcttct ccctgcacca gaagagctgt gtccagcact gccctccagg cttcgccccc    1860

caagtcctcg atacgcacta tagcaccgag aatgacgtgg agaccatccg ggccagcgtc    1920

tgcgccccct gccacgcctc atgtgccaca tgccaggggc cggccctgac agactgcctc    1980

agctgcccca gccacgcctc cttggaccct gtggagcaga cttgctcccg gcaaagccag    2040

agcagccgag agtccccgcc acagcagcag ccacctcggc tgcccccgga ggtggaggcg    2100

gggcaacggc tgcgggcagg gctgctgccc tcacacctgc ctgaggtggt ggccggcctc    2160

agctgcgcct tcatcgtgct ggtcttcgtc actgtcttcc tggtcctgca gctgcgctct    2220

ggctttagtt ttcgggggt gaaggtgtac accatggacc gtggcctcat ctcctacaag      2280

gggctgcccc ctgaagcctg gcaggaggag tgcccgtctg actcagaaga ggacgagggc    2340

cggggcgaga ggaccgcctt tatcaaagac cagagcgccc tctga                    2385
```

<210> SEQ ID NO 3
<211> LENGTH: 794
<212> TYPE: PRT
<213> ORGANISM: Homo sapiens

<400> SEQUENCE: 3

```
Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
            20                  25                  30

Thr Trp Ala Val Arg Ile Pro Gly Gly Pro Ala Val Ala Asn Ser Val
        35                  40                  45

Ala Arg Lys His Gly Phe Leu Asn Leu Gly Gln Ile Phe Gly Asp Tyr
    50                  55                  60

Tyr His Phe Trp His Arg Gly Val Thr Lys Arg Ser Leu Ser Pro His
65                  70                  75                  80

Arg Pro Arg His Ser Arg Leu Gln Arg Glu Pro Gln Val Gln Trp Leu
                85                  90                  95

Glu Gln Gln Val Ala Lys Arg Arg Thr Lys Arg Asp Val Tyr Gln Glu
```

-continued

```
            100                 105                 110

Pro Thr Asp Pro Lys Phe Pro Gln Gln Trp Tyr Leu Ser Gly Val Thr
        115                 120                 125

Gln Arg Asp Leu Asn Val Lys Ala Ala Trp Ala Gln Gly Tyr Thr Gly
    130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
            180                 185                 190

Arg His Gly Thr Arg Cys Ala Gly Glu Val Ala Ala Val Ala Asn Asn
        195                 200                 205

Gly Val Cys Gly Val Gly Val Ala Tyr Asn Ala Arg Ile Gly Gly Val
    210                 215                 220

Arg Met Leu Asp Gly Glu Val Thr Asp Ala Val Glu Ala Arg Ser Leu
225                 230                 235                 240

Gly Leu Asn Pro Asn His Ile His Ile Tyr Ser Ala Ser Trp Gly Pro
                245                 250                 255

Glu Asp Asp Gly Lys Thr Val Asp Gly Pro Ala Arg Leu Ala Glu Glu
            260                 265                 270

Ala Phe Phe Arg Gly Val Ser Gln Gly Arg Gly Gly Leu Gly Ser Ile
        275                 280                 285

Phe Val Trp Ala Ser Gly Asn Gly Gly Arg Glu His Asp Ser Cys Asn
    290                 295                 300

Cys Asp Gly Tyr Thr Asn Ser Ile Tyr Thr Leu Ser Ile Ser Ser Ala
305                 310                 315                 320

Thr Gln Phe Gly Asn Val Pro Trp Tyr Ser Glu Ala Cys Ser Ser Thr
                325                 330                 335

Leu Ala Thr Thr Tyr Ser Ser Gly Asn Gln Asn Glu Lys Gln Ile Val
            340                 345                 350

Thr Thr Asp Leu Arg Gln Lys Cys Thr Glu Ser His Thr Gly Thr Ser
        355                 360                 365

Ala Ser Ala Pro Leu Ala Ala Gly Ile Ile Ala Leu Thr Leu Glu Ala
    370                 375                 380

Asn Lys Asn Leu Thr Trp Arg Asp Met Gln His Leu Val Val Gln Thr
385                 390                 395                 400

Ser Lys Pro Ala His Leu Asn Ala Asn Asp Trp Ala Thr Asn Gly Val
                405                 410                 415

Gly Arg Lys Val Ser His Ser Tyr Gly Tyr Gly Leu Leu Asp Ala Gly
            420                 425                 430

Ala Met Val Ala Leu Ala Gln Asn Trp Thr Thr Val Ala Pro Gln Arg
        435                 440                 445

Lys Cys Ile Ile Asp Ile Leu Thr Glu Pro Lys Asp Ile Gly Lys Arg
    450                 455                 460

Leu Glu Val Arg Lys Thr Val Thr Ala Cys Leu Gly Glu Pro Asn His
465                 470                 475                 480

Ile Thr Arg Leu Glu His Ala Gln Ala Arg Leu Thr Leu Ser Tyr Asn
                485                 490                 495

Arg Arg Gly Asp Leu Ala Ile His Leu Val Ser Pro Met Gly Thr Arg
            500                 505                 510

Ser Thr Leu Leu Ala Ala Arg Pro His Asp Tyr Ser Ala Asp Gly Phe
        515                 520                 525
```

```
Asn Asp Trp Ala Phe Met Thr Thr His Ser Trp Asp Glu Asp Pro Ser
    530                 535                 540

Gly Glu Trp Val Leu Glu Ile Glu Asn Thr Ser Glu Ala Asn Asn Tyr
545                 550                 555                 560

Gly Thr Leu Thr Lys Phe Thr Leu Val Leu Tyr Gly Thr Ala Pro Glu
                565                 570                 575

Gly Leu Pro Val Pro Pro Glu Ser Ser Gly Cys Lys Thr Leu Thr Ser
            580                 585                 590

Ser Gln Ala Cys Val Val Cys Glu Glu Gly Phe Ser Leu His Gln Lys
        595                 600                 605

Ser Cys Val Gln His Cys Pro Pro Gly Phe Ala Pro Gln Val Leu Asp
    610                 615                 620

Thr His Tyr Ser Thr Glu Asn Asp Val Glu Thr Ile Arg Ala Ser Val
625                 630                 635                 640

Cys Ala Pro Cys His Ala Ser Cys Ala Thr Cys Gln Gly Pro Ala Leu
                645                 650                 655

Thr Asp Cys Leu Ser Cys Pro Ser His Ala Ser Leu Asp Pro Val Glu
            660                 665                 670

Gln Thr Cys Ser Arg Gln Ser Gln Ser Ser Arg Glu Ser Pro Pro Gln
        675                 680                 685

Gln Gln Pro Pro Arg Leu Pro Pro Glu Val Glu Ala Gly Gln Arg Leu
    690                 695                 700

Arg Ala Gly Leu Leu Pro Ser His Leu Pro Glu Val Val Ala Gly Leu
705                 710                 715                 720

Ser Cys Ala Phe Ile Val Leu Val Phe Val Thr Val Phe Leu Val Leu
                725                 730                 735

Gln Leu Arg Ser Gly Phe Ser Phe Arg Gly Val Lys Val Tyr Thr Met
            740                 745                 750

Asp Arg Gly Leu Ile Ser Tyr Lys Gly Leu Pro Pro Glu Ala Trp Gln
        755                 760                 765

Glu Glu Cys Pro Ser Asp Ser Glu Glu Asp Glu Gly Arg Gly Glu Arg
    770                 775                 780

Thr Ala Phe Ile Lys Asp Gln Ser Ala Leu
785                 790


<210> SEQ ID NO 4
<211> LENGTH: 4
<212> TYPE: PRT
<213> ORGANISM: Artificial Sequence
<220> FEATURE:
<223> OTHER INFORMATION: Furin consensus recognition site
<220> FEATURE:
<221> NAME/KEY: VARIANT
<222> LOCATION: (2)..(2)
<223> OTHER INFORMATION: X is any amino acid, or no amino acid
<220> FEATURE:
<221> NAME/KEY: VARIANT
<222> LOCATION: (3)..(3)
<223> OTHER INFORMATION: X is Lysine or Arginine

<400> SEQUENCE: 4

Arg Xaa Xaa Arg
1
```